(12) United States Patent
Henry et al.

(10) Patent No.: US 7,833,802 B2
(45) Date of Patent: *Nov. 16, 2010

(54) STROBOSCOPIC LIBERATION AND METHODS OF USE

(75) Inventors: Kent D. Henry, Laramie, WY (US); John Stanley Lovell, Golden, CO (US)

(73) Assignee: ADA Technologies, Inc., Littleton, CO (US)

( * ) Notice: Subject to any disclaimer, the term of this patent is extended or adjusted under 35 U.S.C. 154(b) by 51 days.

This patent is subject to a terminal disclaimer.

(21) Appl. No.: 11/384,172

(22) Filed: Mar. 17, 2006

(65) Prior Publication Data

US 2007/0056388 A1 Mar. 15, 2007

Related U.S. Application Data

(63) Continuation-in-part of application No. 11/081,006, filed on Mar. 14, 2005, now Pat. No. 7,299,679, which is a continuation of application No. 10/719,840, filed on Nov. 21, 2003, now Pat. No. 6,895,804.

(60) Provisional application No. 60/472,386, filed on May 20, 2003, provisional application No. 60/428,531, filed on Nov. 21, 2002, provisional application No. 60/663,292, filed on Mar. 17, 2005, provisional application No. 60/668,264, filed on Apr. 4, 2005.

(51) Int. Cl.
| | |
|---|---|
| *G01J 3/30* | (2006.01) |
| *G01N 21/62* | (2006.01) |
| *G01N 9/00* | (2006.01) |
| *G01N 21/72* | (2006.01) |
| *G01N 23/00* | (2006.01) |
| *G01N 31/12* | (2006.01) |
| *G01N 15/06* | (2006.01) |
| *A61L 2/00* | (2006.01) |
| *C12Q 1/68* | (2006.01) |
| *H05B 37/02* | (2006.01) |
| *B01D 59/44* | (2006.01) |

(52) U.S. Cl. .................... 436/155; 436/171; 436/59; 356/320; 422/78; 422/68.1; 422/23; 250/494.1; 250/390.04; 250/282; 435/6; 315/224; 73/31.05; 313/154

(58) Field of Classification Search ................. 436/171, 436/59, 155; 356/320; 422/78, 68.1, 23; 250/494.1, 390.04, 282; 435/6; 315/224; 73/31.05; 313/154
See application file for complete search history.

(56) References Cited

U.S. PATENT DOCUMENTS 3,463,591 A * 8/1969 Cross et al. ................ 356/318

(Continued)

FOREIGN PATENT DOCUMENTS

| EP | 0485425 | 5/1992 |
|---|---|---|
| WO | 9427145 | 11/1994 |
| WO | WO 99/01750 | 1/1999 |

OTHER PUBLICATIONS

Fryer et al., "Dependence of the Glass Transition Temperature of Polymer Films on Interfacial Energy and Thickness," 2001, Macromolecules, vol. 37, No. 16, pp. 5627-5634.

(Continued)

*Primary Examiner*—Lore Jarrett
(74) *Attorney, Agent, or Firm*—Sheridan Ross P.C.

(57) ABSTRACT

The invention is directed to a system and method for detecting substances, such as explosives and/or drugs, using, in part, short bursts of energy light from a relatively low energy strobe. Embodiments include coupling the strobe with a detector for use in a portable hand-held unit, or a unit capable of being carried as a backpack. Embodiments further include placement of one or more stroboscopic desorption units and detectors in luggage conveyors systems, carry-on X-ray machines, and check-in counter locations.

21 Claims, 12 Drawing Sheets

U.S. PATENT DOCUMENTS

| | | | |
|---|---|---|---|
| 3,680,959 A * | 8/1972 | Schuch et al. | 356/313 |
| 3,748,905 A | 7/1973 | Fletcher et al. | |
| 3,853,503 A * | 12/1974 | Folmer, Jr. | 95/84 |
| 4,040,411 A * | 8/1977 | Rust | 126/602 |
| 4,580,440 A | 4/1986 | Reid et al. | |
| 4,718,268 A | 1/1988 | Reid et al. | |
| 4,754,655 A | 7/1988 | Parker et al. | |
| 4,819,477 A | 4/1989 | Fisher et al. | |
| 4,820,920 A | 4/1989 | Bather | |
| 4,867,796 A | 9/1989 | Asmus et al. | |
| 4,982,176 A * | 1/1991 | Schwarz | 340/567 |
| 5,017,780 A * | 5/1991 | Kutscher et al. | 250/287 |
| 5,092,155 A | 3/1992 | Rounbehler et al. | |
| 5,092,157 A | 3/1992 | Achter et al. | |
| 5,092,218 A | 3/1992 | Fine et al. | |
| 5,092,220 A * | 3/1992 | Rounbehler | 89/1.1 |
| 5,112,127 A | 5/1992 | Carrabba et al. | |
| 5,122,127 A | 6/1992 | Stanley | |
| 5,138,889 A | 8/1992 | Conrad | |
| 5,147,611 A * | 9/1992 | Stout et al. | 422/78 |
| 5,149,972 A | 9/1992 | Fay et al. | |
| 5,278,418 A | 1/1994 | Broadhurst | |
| 5,476,794 A | 12/1995 | O'Brien et al. | |
| 5,580,733 A * | 12/1996 | Levis et al. | 435/6 |
| 5,585,575 A | 12/1996 | Corrigan et al. | |
| 5,600,700 A | 2/1997 | Krug et al. | |
| 5,663,561 A | 9/1997 | Franzen et al. | |
| 5,693,152 A | 12/1997 | Carron | |
| 5,751,897 A | 5/1998 | Van Alstyne | |
| 5,782,253 A * | 7/1998 | Cates et al. | 134/105 |
| 5,842,995 A | 12/1998 | Mahadevan-Jansen et al. | |
| 5,859,375 A | 1/1999 | Danylewych-May et al. | |
| 5,862,273 A | 1/1999 | Pelletier | |
| 5,904,900 A | 5/1999 | Bleuse et al. | |
| 5,942,699 A | 8/1999 | Omath et al. | |
| 5,955,729 A * | 9/1999 | Nelson et al. | 250/282 |
| 5,965,884 A | 10/1999 | Laiko et al. | |
| 5,972,638 A * | 10/1999 | Burlage et al. | 435/29 |
| 6,018,389 A | 1/2000 | Kyle et al. | |
| 6,085,601 A | 7/2000 | Linker et al. | |
| 6,191,406 B1 * | 2/2001 | Nelson et al. | 250/208.1 |
| 6,353,476 B1 | 3/2002 | Allen et al. | |
| 6,446,514 B1 | 9/2002 | Danylewych-May et al. | |
| 6,477,907 B1 | 11/2002 | Chambers et al. | |
| 6,558,626 B1 | 5/2003 | Aker et al. | |
| 6,558,956 B1 | 5/2003 | Carron et al. | |
| 6,614,523 B1 * | 9/2003 | Boss et al. | 356/301 |
| 6,621,574 B1 | 9/2003 | Forney et al. | |
| 6,692,694 B1 | 2/2004 | Curry et al. | |
| 6,723,564 B2 * | 4/2004 | Hillenkamp | 436/94 |
| 6,730,923 B1 * | 5/2004 | May et al. | 250/494.1 |
| 6,734,423 B2 | 5/2004 | Bryden | |
| 6,735,368 B2 | 5/2004 | Parker et al. | |
| 6,753,396 B2 | 6/2004 | Ulbricht et al. | |
| 6,775,448 B2 | 8/2004 | Zoorob | |
| 6,788,863 B2 | 9/2004 | Parker et al. | |
| 6,797,242 B2 | 9/2004 | Neumann et al. | |
| 6,797,944 B2 | 9/2004 | Nguyen et al. | |
| 6,828,795 B2 | 12/2004 | Krasnobaev et al. | |
| 6,838,663 B2 | 1/2005 | Coon et al. | |
| 6,856,737 B1 | 2/2005 | Parker et al. | |
| 6,861,646 B2 | 3/2005 | Motchkine et al. | |
| 6,870,155 B2 | 3/2005 | Krasnobaev et al. | |
| 6,888,128 B2 | 5/2005 | Krasnobaev et al. | |
| 6,895,804 B2 * | 5/2005 | Lovell et al. | 73/31.05 |
| 6,897,951 B2 | 5/2005 | Womble et al. | |
| 6,947,132 B1 | 9/2005 | Boss et al. | |
| 6,959,127 B2 | 10/2005 | Zoorob | |
| 6,967,717 B1 | 11/2005 | Boss et al. | |
| 7,016,586 B2 | 3/2006 | Zoorob et al. | |
| 7,027,701 B2 | 4/2006 | Parker et al. | |
| 7,084,397 B2 | 8/2006 | Hirano et al. | |
| 7,116,878 B2 | 10/2006 | Zoorob et al. | |
| 7,162,132 B2 | 1/2007 | Parker et al. | |
| 7,244,288 B2 | 7/2007 | Belyakov et al. | |
| 7,248,770 B2 | 7/2007 | Parker et al. | |
| 7,299,679 B2 * | 11/2007 | Lovell et al. | 73/31.05 |
| 7,574,930 B2 | 8/2009 | Bunker | |
| 7,576,320 B2 | 8/2009 | Bunker et al. | |
| 2003/0039299 A1 | 2/2003 | Horovitz et al. | |
| 2003/0133105 A1 | 7/2003 | Gorelik et al. | |
| 2003/0155504 A1 | 8/2003 | Motchkine et al. | |
| 2003/0230152 A1 | 12/2003 | McGill et al. | |
| 2004/0157342 A1 | 8/2004 | Lovell et al. | |
| 2005/0007119 A1 | 1/2005 | Belyakov et al. | |
| 2005/0047702 A1 | 3/2005 | Parker et al. | |
| 2005/0079626 A1 | 4/2005 | Kunz | |
| 2005/0235739 A1 | 10/2005 | Lovell et al. | |
| 2005/0248758 A1 | 11/2005 | Carron et al. | |
| 2006/0062540 A1 | 3/2006 | Zoorob et al. | |
| 2006/0119853 A1 | 6/2006 | Baumberg et al. | |
| 2006/0219937 A1 * | 10/2006 | Henry et al. | 250/425 |
| 2006/0228251 A1 * | 10/2006 | Schneberger et al. | 422/23 |
| 2006/0256340 A1 | 11/2006 | Hansen et al. | |
| 2007/0015288 A1 | 1/2007 | Hulteen et al. | |
| 2007/0215725 A1 | 9/2007 | Bunker | |
| 2008/0290810 A1 * | 11/2008 | Kiernan et al. | 315/224 |

OTHER PUBLICATIONS

"2,4—Dinitrotoluene Material Safety Data Sheet," Sep. 1997, Toxic Air Contaminant Identification Series, pp. 437-439.

Lewis, J., "Recommendation to List 2,4,6—Trinitrotoluene (TNT) as a Potential Pollutant," Apr. 2001, pp. 1-8.

PCT—Notification of Transmittal of the International Search Report and the PCT International Search Report dated Jun. 22, 2004.

Paul Tompkins et al.; "Icebreaker: An Exploration of the Lunar South Pole," copyright 1999 by the Space Studies Institute, 11 pages.

V.A. Morosov et al.; "2π spectrometer: A new apparatus for the investigation of ion surface interaction," Rev. Sci. Instrum. 67(6) (Jun. 1996), pp. 2163-2170.

Yvan Simard et al.; "New technology for the detection of micronekton: multivariate acoustics, sampling and data analysis strategies," printed Nov. 13, 2003, 24-pages, available at http://pulson.seos.uvic.ca/meeting/scor2000/simard/simard.html.

V. Debur et al.; "Position-sensitive detector for the 6-meter optical telescope," printed Nov. 13, 2003, 6 pages, available at http://arxiv.org/pdf/astro-ph/0310353.

K. Fransson; "The Trigger System of the CELSIUS/WASA Detector," Physica Scripta T99, (2002), pp. 176-182.

M. Mayer et al.; "Performance of CdZnTe Strip Detectors as Submillimeter Resolution Imaging Gamma Radiation Spectrometers," undated, 5 pages.

U.S. Appl. No. 12/020,419, filed Jan. 25, 2008, Henry et al.

Prism (optics), Wikipedia, the free encyclopedia, available at http://en.wikipedia.org/wiki/Prism_%28optics%29, printed Jan. 18, 2008, pp. 4.

Optical instruments—Wikipedia, the free encyclopedia, available at http://en.wikipedia.org/wiki/Optical_instrument, printed Jan. 18, 2008, pp. 2.

Lens (optics)—Wikipedia, the free encyclopedia, available at http://en.wikipedia.org/wiki/Lens_%28optics%29, pp. 15.

Mirror—Wikipedia, the free encyclopedia, available at http://en.wikipedia.org/wiki/Mirror, printed Jan. 18, 2008, pp. 11.

Internet web page for Mesophotonics regarding Klarite, available at http://www.mesophotonics.com/products/klarite.html, cite updated May 4, 2007, pp. 1-2.

Kambhampati, et al., "On Chemical Mechanism of Surface Raman Scattering: Experiment and Theory", Chem. Phy. 1998(108): 5013-5026.

Background for the above-captioned application (previously provided).

Handschh, Martin, et al., Laser-induced molecular desorption and particle ejection fromorganic films, 1999, Applied Surface Science, vol. 137, pp. 125-135.

Kawai et al. "Application Note #18: Raman Spectroscopy for Homeland Defense Applications" by InPhotonics, 2004, pp. 1-4.

Thiesan et al., "Survey of Commercially Available Explosives Detection Technologies and Equipment 2004", Sandia National Laboratories, Document No. 208861, Feb. 2005, 97 pages.

"Global Security Solutions" available at http://www.global-security-solutions.com/, printed Sep. 11, 2009.

* cited by examiner

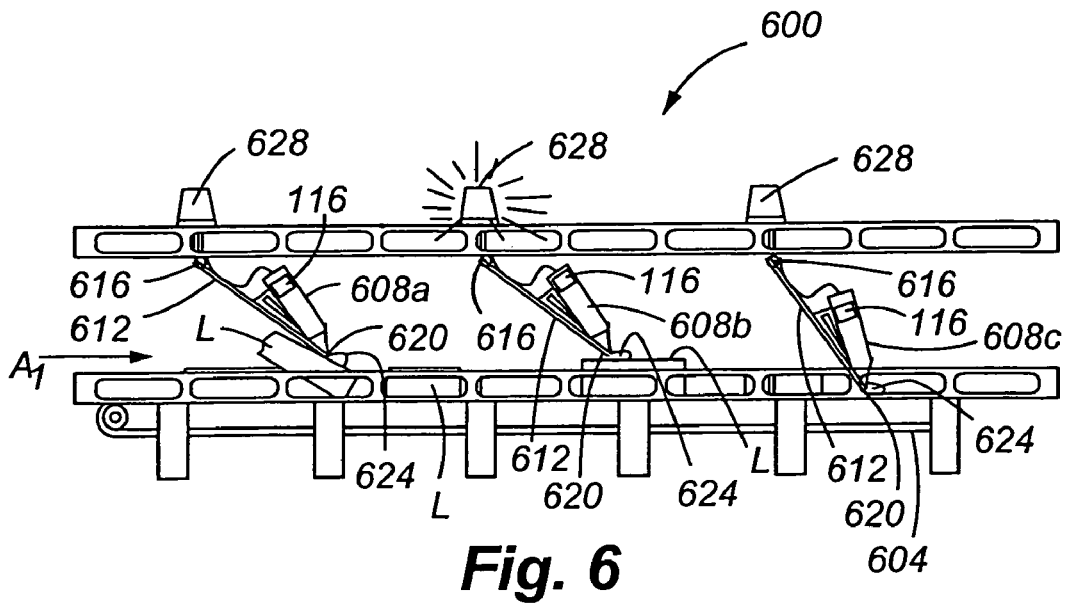
Fig. 6
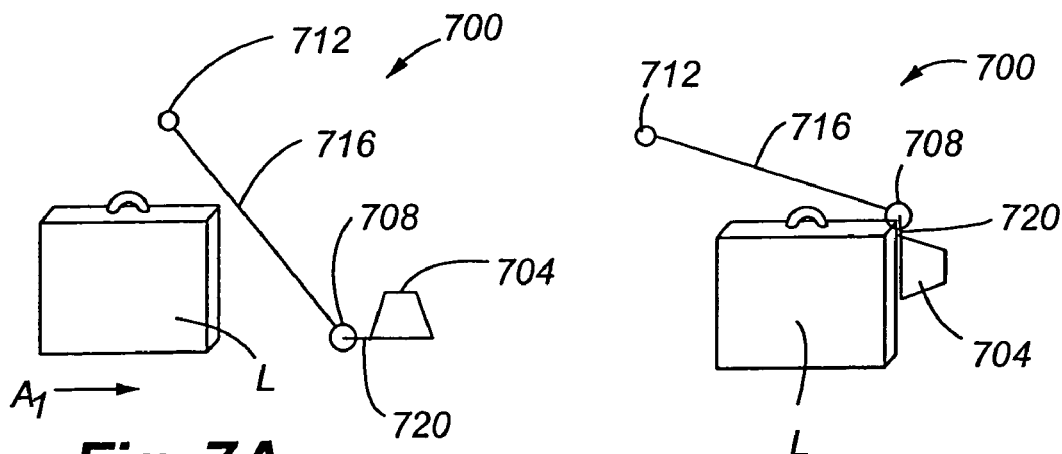
Fig. 7A
Fig. 7B
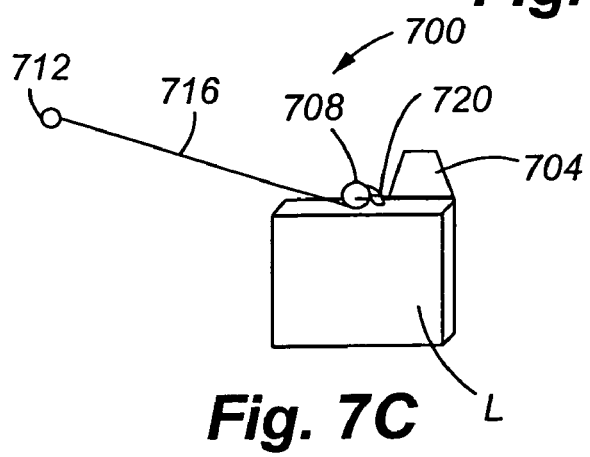
Fig. 7C

FIG. 9B
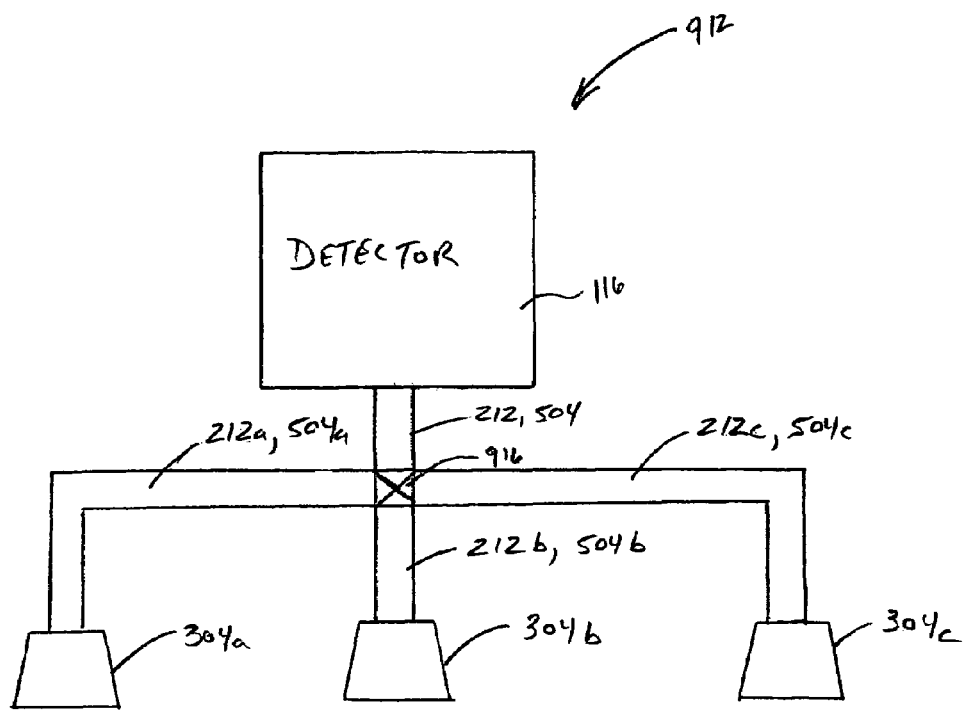
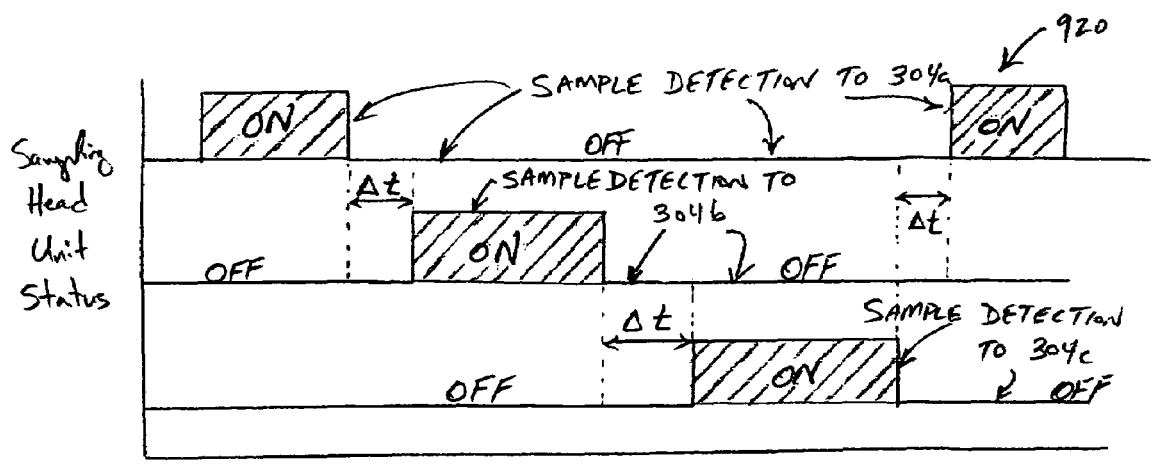
FIG. 9C

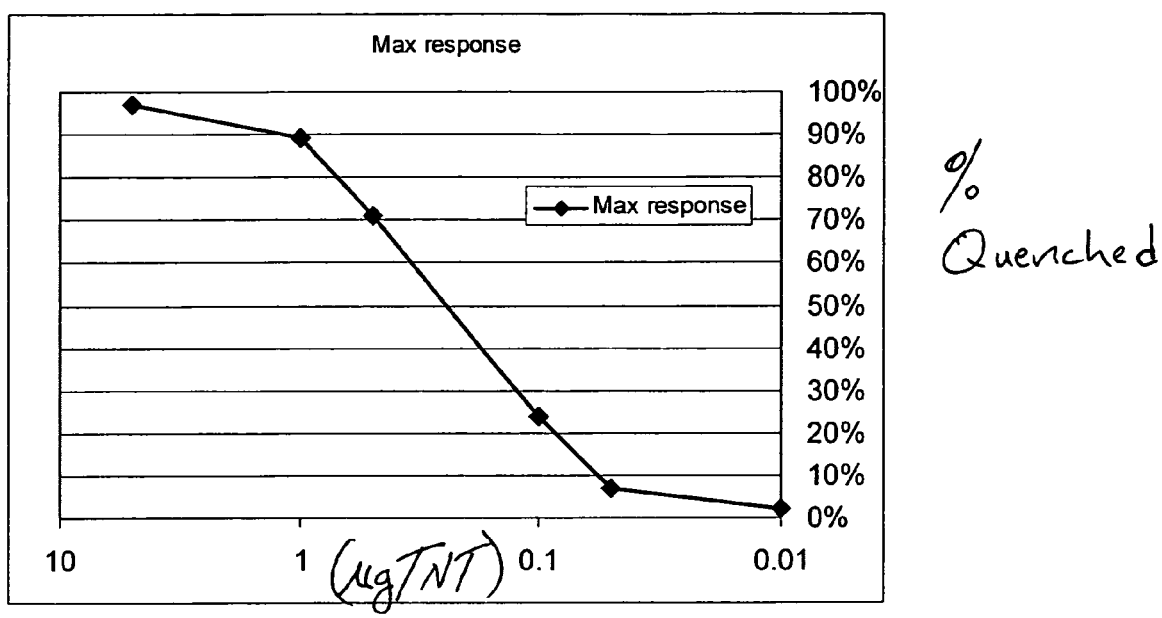
Figure 16: Fluorescent polymer sensor response to TNT

STROBOSCOPIC LIBERATION AND METHODS OF USE

CROSS-REFERENCE TO RELATED APPLICATIONS

The present application is a continuation-in-part application of U.S. patent application Ser. No. 11/081,006 filed Mar. 14, 2005, now U.S. Pat. No. 7,299,679 entitled "Strobe Desorption Method for High Boiling Point Materials", which is a continuation application of U.S. patent application Ser. No. 10/719,840 filed on Nov. 21, 2003 entitled "Strobe Desorption Method for High Boiling Point Materials" (now U.S. Pat. No. 6,895,804 issued on May 24, 2005), which claimed the benefit of U.S. Provisional Patent Application Nos. 60/472,386 filed May 20, 2003 and 60/428,531 filed Nov. 21, 2002; in addition, the present application claims the benefit of U.S. Provisional Patent Application No. 60/663,292 filed Mar. 17, 2005 entitled "Stroboscopic Desorption IP/Landmine", and U.S. Provisional Patent Application No. 60/668,264 filed Apr. 4, 2005 entitled "Automatic Baggage Screening for Explosives and Narcotics". The contents of the applications listed above are incorporated herein by reference in their entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of W911 QX-04-C-0006 awarded by the U.S. Army.

FIELD

The present invention is related to a device and method for liberating a sample from an article using a light pulse, and in at least one embodiment, a relatively low-power strobe light is used for stroboscopic liberation or desorption of compounds and/or particles of interest.

BACKGROUND

Explosives and other controlled substances, such as drugs, have become major societal problems. Increasingly, terrorist acts using explosives are becoming a problem not only for countries in the Middle East but also for Western countries in other parts of the world. Explosives constitute a weapon used by terrorists and insurgents, wherein the explosives may be hidden in a myriad of devices; however, it is typically difficult for a person handling explosives to avoid contamination after coming into contact with an explosive or explosive device because explosives readily adhere to surfaces.

In addition to explosives, drug abuse has been a longstanding problem for Western countries and consumes large amounts of law enforcement resources each year. Canines, metal detectors, and "sniffer" detectors have been used at various locations, such as airports, border crossings, and the like to detect explosive devices and illegal drugs. These measures have had mixed success.

Another measure that has been employed to detect contraband substances has been to collect loose particles from surfaces or skin with a vacuum cleaner or a swipe. The swipe or the particles collected by the vacuum are then heated to release the vaporizable material for analysis. This approach is in routine use at airports throughout the world for screening airline passengers. An example of such a system is the Barringer™ Ion Scan System™; however, this technique has drawbacks. For example, the use of swipes or particle vacuums is an intermittent process, which requires manual intervention between the sampling and analysis. This is a time consuming approach that is inherently slow, although it may optionally be used in conjunction with at least one embodiment of the present invention.

Previously disclosed devices for volatilizing certain substances for detection include a high-energy apparatus disclosed in U.S. Pat. No. 6,895,804. The content of U.S. Pat. No. 6,895,804 is incorporated herein by reference in its entirety. The landmine detection apparatus of the '804 patent applies a relatively high amount of energy to the sample target that is generally intended to be soil. To provide the requisite energy, the radiation source of the '804 patent is powered by a relatively high amount of energy, and therefore, is limiting in its ability to serve as a self-contained backpack unit, handheld device, or other relatively compact portable device. In addition, high-energy strobes are slow to recharge, utilize kilowatts of energy to power, and are heavy as a self-contained unit that includes a power source.

U.S. Pat. No. 6,828,795, incorporated herein by reference, suggests use of an ion mobility spectrometer with a heat source, but energy levels have not been provided. U.S. Patent Application Publication No. 2005/0007119 A1, related to the '795 patent, is also incorporated herein by reference. The '795 patent discloses using an electrostatic precipitator to take out particulates, presumably to keep them out of the ion mobility spectrometer. It is noted here that, in at least one embodiment, the present invention advantageously releases a plume of particulates that is then able to form at least part of the signal.

As noted above, present techniques for airport security include sometimes screening baggage for trace explosives by manually swiping the surface of the baggage and analyzing the swipe, such as by using Ion Mobility Spectrometry. Not all bags are tested for trace explosives, with carry-on baggage typically being X-rayed but not always screened for traces of explosives. Thus, there would be an advantage to automatically screening all baggage, whether checked or carry-on, for explosives. In addition, upon arrival at a destination airport, government agencies at the destination airport typically also screen baggage, wherein such screen efforts typically include searches for drugs. Thus, it would be advantageous to be able to automatically screen baggage upon arrival, such as when baggage is unloaded from international flights. Accordingly, among other types of screening uses, such as crime scene analysis, there is clearly a need for automatically screening airline baggage and carry-on items for traces of explosives and drugs.

SUMMARY

In one embodiment, the present invention is directed to a relatively low-energy system and associated methods for detecting substances, such as high boiling point and low vapor pressure materials, using energy radiation imparted by a suitable radiation source, such as a relatively low energy strobe, over a short time period. Examples of substances that are detectable include explosives and other controlled substances, such as drugs and chemical warfare agents. "Explosives" refer to a chemical compound, usually containing nitrogen, that detonate or deflagrate as a result of shock or heat. "Drugs" refer to a substance that acts on the central nervous system, e.g., a narcotic, hallucinogen, barbiturate, or psychotropic drug. "Chemical warfare agents" refer to chemical compounds designed kill, injure or incapacitate persons.

The sampling of vapor comprises gas-phase molecules that are emitted from a solid or liquid. The concentration of target substances in the air is related to the vapor pressure of the target substance and to other factors such as the amount of time the target substance is present in a location, its affinity to local substrates, its packaging, air circulation in the location, etc. The sampling of particulate matter is also possible and may be facilitated by stroboscopic desorption. Here, microscopic particles of the solid target substance or non-target substance to which the target substance is attached is sampled. For example, explosives material that adheres to surfaces such as by direct contact with the explosive, or indirectly, through contact with someone's hands who has been handling explosives.

The target material can be a variety of possible substances, including a semi-volatile co-contaminant or a high boiling point and/or low vapor pressure material or a derivative thereof. Typically, a high boiling point material has a boiling point of at least about 150° C., more typically of at least about 250° C., and a low vapor pressure material is a material having a vapor pressure of no more than about $2 \times 10^{-3}$ mmHg and more typically of no more than about $2 \times 10^{-4}$ mm Hg under conditions of standard temperature and pressure (STP). The derivative can itself be a high boiling point and/or low vapor pressure material. Typical substances of interest include at least one of an explosive compound, an explosive related compound, a chemical warfare agent, a drug, an industrial compound or toxic industrial compound (TIC), and derivatives thereof. Examples of TNT derivatives include dinitrotoluene, 2-ADNT and 4-ADNT. Such derivatives can be unique markers to the presence of the source substance. Examples of target materials include explosives, such as TNT, nitroglycerine, ammonium nitrate, acetylides of copper and/or silver, mercury fulminate, lead azide, diazodinitrophenol, nitrosoguanidine, lead styphnate, cyclotrimethylenetrinatramine or RDX, pentaerythritol tetranitrate or PETN, triacetone triperoxide or TATP, dynamite, semtex, EGDN, DMNB, H-6, C-4, picric acid, nitrocellulose, and illicit drugs such as cocaine, heroin, opium, marijuana, methamphetamines, LSD, and co-contaminants from the manufacturer or purification of these drugs.

The sample area can be any suitable animate or inanimate surface. The methods provided herein have particular application to the detection of substances for security and drug enforcement operations. Accordingly, the sample area can be a variety of surfaces, including, but not limited to, the skin of a body part, such as a hand, clothing, shoes, documents including travel documents, currency, weapons and weapon components, luggage, bags, mail, packages, envelopes, metal, glass, plastic and painted surfaces, refuse, biological or biological related matter, vehicles, cargo containers, furniture surfaces, flooring, wood and canvas.

In accordance with some embodiments of the present invention, liberation of target substances can be achieved by using extremely short bursts of energy light in the form of stroboscopic desorption. When used in combination with a detector, this liberation technology is termed stroboscopic signal amplification. By using stroboscopic signal amplification, the detection limits of a traditional trace vapor detector may be increased by two or more orders of magnitude over a traditional trace vapor detector that does not use stroboscopic signal amplification. Accordingly, as a result of the mechanism of stroboscopic signal amplification, the vapor mode detection of currently available instrumentation is able to momentarily sample both an enhanced vapor concentration and liberated particles from the surface under study. Thus by employing stroboscopic enhanced trace chemical detection, there is less reason to operate a trace chemical detector in particle mode employing the manual steps employing a swipe, although a swipe could first be performed if desired. For example, a swipe could be obtained from inside a relatively small container, such as a narrow tube, and then the swipe tested, such as by using stroboscopic signal amplification and an associated detector. To work most efficiently with stroboscopic signal amplification, the trace detector should have an optimized vapor inlet that prevents condensation of low vapor pressure compounds and entrapment of particulates before being either directly detected or deposited on the detector's internal preconcentrator.

Advantageously, strobe desorption can liberate explosive- and/or drug-bearing particulates from surfaces for detection. Low-energy strobes provide an attractive radiation source for liberating a sample from an article because they have a low capacity for heating with minimal to negligible heating of the sample substrate. That is, the heating from a low-energy strobe is sufficient to cause some vaporization or physical liberation through plume generation of target constituents on the surface of the article, but less heating of the sample substrate relative to a high-energy strobe. As a result, the low energy strobe of the present invention is suitable for operating on a wide range of articles, wherein the low energy strobe yields acceptably low or negligible heat damage to the subject articles. In addition, low energy strobes are relatively fast to recharge, use watts (versus kilowatts) of energy and light, and are suitable for use in relatively compact configurations, including battery operated backpack and/or handheld sampling devices. Accordingly, as those skilled in the art will appreciate, the present invention has application to a wide variety of uses, including personnel screening, such as at transportation facilities, large public gathering places, political events, and prisoner intake. In addition, as further illustrated herein, embodiments of the present invention have application to screening objects, such as clothing, footwear, baggage, vehicles, containers, packages, mail and documents.

Some embodiments of the present invention are directed at obtaining samples of compounds from a sample surface, such as those articles mentioned directly above. Those skilled in the art will appreciate that high amounts of energy imparted to the sample surface can generate an airborne sample to achieve this goal. Difficulty exists in providing a relatively low power mechanism that does not burn or otherwise appreciably damage the sample surface. However, a minimum value of energy, as described herein, is necessary in order to assist in desorption or liberation of particles or compounds from the sample surface. Accordingly, in at least one embodiment of the invention, a strobe light is provided, wherein a relatively short burst of light is directed to the sample surface, the energy from the light causes some heating of the surface to vaporize some types of compounds (low vapor pressure compounds) and/or generates a relatively small heat shock to the sample surface that creates a plume, thereby lifting particles. However, the heating of the sample surface is not enough to cause damage to surfaces typically encountered on luggage, travel documents, clothing, or even skin. Thus, in accordance with embodiments of the present invention, the stroboscopic source provides a non-pyrolizing apparatus for liberating a material from a sample surface, although the detector mechanism may incorporate a pyrolizing apparatus once the sample is collected. In accordance with embodiments of the present invention, the stroboscopic source may also provide desorption of non-target components, thereby liberating target substances.

In a separate aspect of the invention, deployment of a stroboscopic desorption and associated detection device can be used to automatically screen luggage, packages and/or a variety of articles. In some embodiments of the invention, stroboscopic desorption and detection is conducted during pick-up and or conveyance of the luggage or packages, such as along a conveyor belt that carries the luggage to the intended airplane or other mode of transportation (such as train, ship, or vehicle). Such screening system may be used, as for example, in an the vicinity of an existing X-ray machine, thereby allowing all of the baggage to be screened for explosives or other target substances, with little or no increase in personnel. The invention can also be applied to automatically screen baggage for illicit drugs as it is unloaded from international flights prior to customs.

Thus, in one embodiment of the invention, a system for detecting at least one chemical located on a sample surface is provided, the system comprising a first strobe for imparting an energy to the sample surface, the first strobe providing between about 0.4 to 5 Joules of energy per square centimeter of the sample surface area as measured at the sample surface, wherein the energy liberates the at least one chemical from the sample surface. In addition, the system comprises a detector, a detector mechanism, or a means means for detecting the at least one chemical upon liberation by the energy. In accordance with some embodiments of the present invention, at least a portion of the energy is transmitted to the sample surface during an initial discharge peak interval of less than about 100 microseconds. In addition, in accordance with one or more embodiments, the first strobe is powered by at least one battery, such as a 6-volt dc battery. In addition, in accordance with one or more embodiments of the invention, the first strobe is positioned within a reflector, the reflector having a parabolic shape in side profile, the parabolic shape described by an equation $x^2=4py$, wherein p equals at least one half of the diameter of a flash lamp portion of the strobe. In accordance with some embodiments, the means for detecting further comprises means for sampling at least one of an airborne particle and compound associated with the at least one chemical. Furthermore, in one or more embodiments, the means for sampling comprises at least one of a pump and a fan. In some embodiments, the means for detecting comprises a fiber optic. In one or more embodiments, the means for detecting is selected from the group consisting of spectroscopy, thermo-redox, chemiluminescence, and spectrometry, and in one or more embodiments, the means for detecting comprises surface enhanced Raman spectroscopy. In accordance with some embodiments of the invention, the system may further comprise a second strobe located proximate the first strobe and directed at the sample surface, and one or more embodiments, the first and second strobes may be operatively associated with a common shroud. In yet other embodiments, the system is operatively associated with a conveyance mechanism for moving the sample surface from a first position to a second position, wherein the first position is not in sampling proximity of the first strobe and wherein second position is in sampling proximity with the first strobe. In addition, in one or more embodiments, the first strobe is interconnected to a hand wand, the hand wand spaced apart from at least a portion of the means for detecting. In other embodiments, the first strobe is interconnected to sampling head, the sampling head operatively associated with at least one of a handle, a hand wand, a check-in counter, an X-ray machine, a conveyor belt, a biasing member, and a hinged arm. In addition, in one or more embodiments, the means for detecting comprises a preconcentrator.

In some embodiments of the invention, a system for detecting at least one of an explosive, an explosive related compound, a chemical warfare agent, a toxic industrial compound, a drug, and derivatives thereof is provided, the system comprising at least one strobe, wherein the strobe emits a pulse of light to a sample surface comprising the explosive, explosive related compound, chemical warfare agent, toxic industrial compound, drug, and/or derivatives thereof, the pulse of light providing an energy at the sample surface of between about 0.4 to 5 Joules per square centimeter of the sample area. In addition, the system comprises a sampling mechanism operatively associated with the strobe, wherein the sampling mechanism samples the air proximate the sample surface. In addition, the system comprises a detector communicating with the sampling mechanism. The system may further comprise other features as described herein.

In some embodiments of the invention, a trace chemical luggage detection system for detecting at least one of an explosive, an explosive related compound, a chemical warfare agent, a toxic industrial compound, a drug, and derivatives thereof, from a luggage surface is provide, the system comprising at least one strobe, wherein the strobe emits an energy pulse of light to the luggage surface, a sampling mechanism operatively associated with the strobe, wherein the sampling mechanism samples the air proximate the luggage surface, and a detector communicating with the sampling mechanism. In one or more embodiments of the invention, at least a portion of the energy pulse is transmitted to the luggage surface during an initial discharge peak interval of less than about 100 microseconds. In addition, in some embodiments of the invention, the first strobe is interconnected to a sampling head, the sampling head operatively associated with at least one of a handle, a hand wand, a check-in counter, an X-ray machine, a conveyance mechanism, a floor, a sample container, a vehicle, a flap, a conveyor belt, a biasing member, and a hinged arm. In at least some embodiments of the invention, the first strobe is positioned within a reflector, the reflector having a parabolic shape in side profile, the parabolic shape described by an equation $x^2=4py$, wherein p equals at least one half of the diameter of a flash lamp of the strobe. In at least one embodiment of the invention, the system is operatively associated with a conveyance mechanism for moving the sample surface from a first position to a second position, wherein the first position is not in sampling proximity of the first strobe and wherein second position is in sampling proximity with the first strobe. In some embodiments of the invention, the energy pulse of light is between about 0.4 to 5 Joules per square centimeter at the luggage surface. The system may further comprise other features as described herein.

Some embodiments of the present invention are also directed to methods of detecting a chemical. Accordingly, in an embodiment of the present invention, a method for detecting a trace chemical from a sample surface is provided, the method comprising: (a) pulsing a strobe directed at the sample surface, the strobe imparting an energy to the sample surface of between about 0.4 to 5 Joules of energy per square centimeter of the sample surface area as measured at the sample surface, wherein the energy liberates a material from the sample surface; (b) collecting the material in an airborne sample; and (c) detecting the trace chemical from the material. In addition, in at least one embodiment, the material comprises one or more of a particle and a compound in the airborne sample. In another embodiment, the method may further comprise moving the sample surface under the strobe prior to the pulsing step. In addition, in an embodiment of the method, the collecting step comprises the substep of providing a at least one of a pump and a fan to pull the material toward at least a portion of a detector before the detecting step. In another embodiment, the method may further comprise activating an alarm after the detecting step. In some embodiments, at least one of the collecting and the detecting steps comprise the substep of transporting the collected sample through a heated conduit to a detector. In an embodiment of the method, at least a portion of the energy is transmitted to the sample surface during an initial discharge peak interval of less than about 100 microseconds. In addition, in one or more embodiments, the trace chemical comprises a high boiling point and/or low vapor pressure, and wherein the trace chemical comprises is at least one of an explosive, an explosive related compound, a chemical warfare agent, a drug, a toxic industrial compound, and derivatives thereof. In one or more embodiments of the invention, the collecting step comprises the substep of conveying the airborne sample to a preconcentrator, and the substep of conveying may further include conveying a plurality of airborne samples to the preconcentrator before the step of detecting.

Various embodiments of the present invention are set forth in the attached figures and in the detailed description of the invention as provided herein and as embodied by the claims. It should be understood, however, that this Summary may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIGS. 6-9A are views of various automated stroboscopic sampling systems in accordance with embodiments of the present invention;

FIG. 9B is a schematic of a portion of an embodiment of a detection apparatus with a plurality of sample heads and a means for conveying sample or sample information to an associated detector;

FIG. 9C is a graph illustrating an "on/off" timing configuration for using multiple sampling heads for an embodiment of the present invention;

FIG. 16 is a plot of percent quenched (vertical axis) versus sample concentration of TNT in units of micrograms (horizontal axis) for an experiment as discussed in Example 3 herein.

DETAILED DESCRIPTION

In accordance with embodiments of the invention, a radiation source is provided for liberation or desorption of material from a sample. The present invention preferably utilizes a strobe for providing the radiation source, thereby yielding a stroboscopic signal amplification device that can be used with a variety of different types of detectors, as discussed in more detail below. In general, the strobe provides a non-damaging discharge of energy over a relatively very short period of time, such as on the order of several hundreds of microseconds for the total light pulse. This results in a discharge from the strobe that takes relatively very little power, but releases a substantial amount of energy. The light energy from the strobe is directed toward the target surface, where the sample surface may comprise, such as by way of example and not limitation, a surface of a piece of luggage, package, skin surface, fabric surface, currency or document.

Stroboscopic desorption is believed to provide signal amplification via two mechanisms. First, energy from the strobe heats the surface to increase the vapor pressure of high boiling point (low vapor pressure) compounds, thereby placing vapors of the compounds into the airspace above the sample surface. Second, mechanical shock generated by the strobe creates a plume of micron and sub-micron particles from the surface. The shock comes in two separate parts: (a) rapid expansion of heated air at the flash lamp interface with the atmosphere; and (b) rapid absorption of energy at the illuminated medium causing the ejection of particulates from the target surface. In general, particle liberation is due to the shock associated with the energy absorption at the sample surface and not from the heating of the air in the vicinity of the flash tube. Indeed, the present invention can function even if a piece of glass is placed between the strobe and the target surface. Therefore, the mechanism for liberating the sample from the target surface is a function of the coupling of the light generated by the strobe and the absorption of light by the target surface.

One advantage of the present invention is that it does not rely on the use of ultrasonic vibrations, air bursts, and/or continuous infrared or continuous visible spectrum light illumination (which is very power intensive) to liberate the sample from the target surface, although one or more of these features, such as air bursts, could be used with the present invention. Because the power requirements of the present invention are relatively low, the strobe of the present invention may be powered on direct current batteries, such as AA batteries, D cell batteries, lithium or nickel metal hydrides, or other comparable battery packs. This directly contrasts with stroboscopic desorption systems of the prior art that use relatively large amounts of power.

Figure 1:
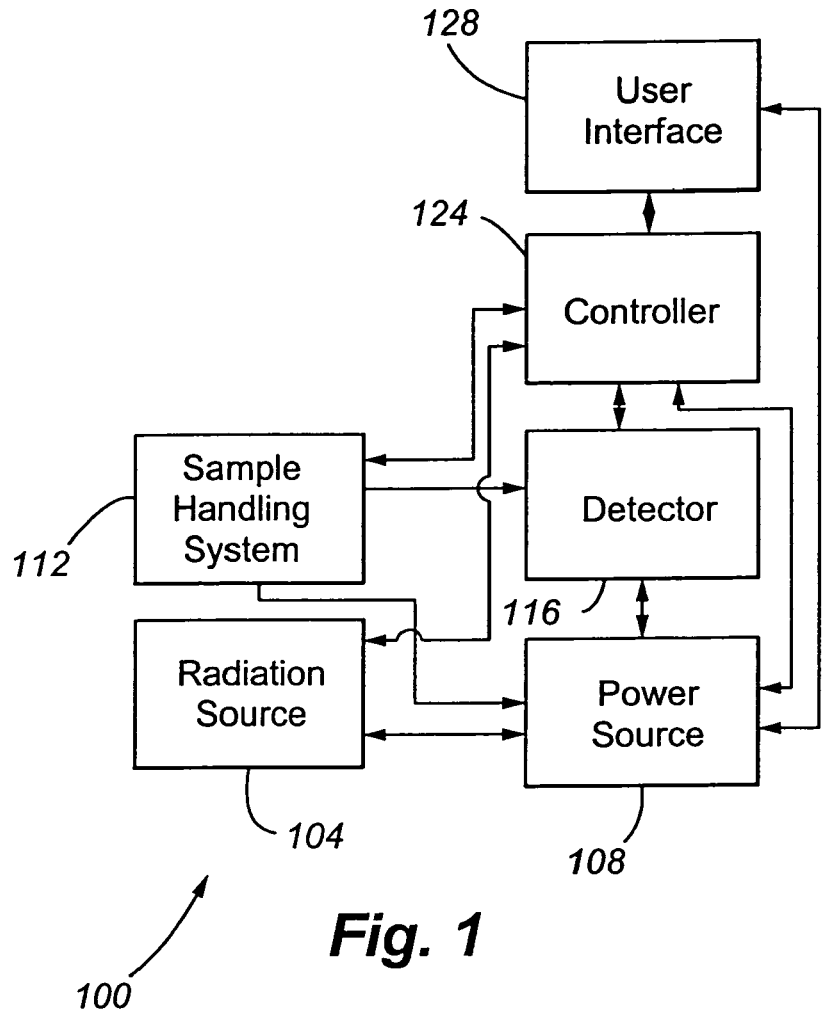
FIG. 1 is block diagram depicting components of a system in accordance with embodiments of the present invention.

A first possible embodiment of a detection system of the present invention is depicted in FIG. 1. The detection system 100 includes a radiation source 104, a power source 108, a sample handling system 112, a detector 116, a controller 124, and a user interface 128. The detection system 100 illuminates a sample area with radiation emitted by the radiation source 104, transports a sample collected at or near the sample area using the sample handling system 112 to the detector 116, and measures the concentration of or otherwise detects the presence of one or more target substances using the detector 116. The sample contains liberated and/or volatilized materials, including the target material(s) to be detected, if present.

Referring again to FIG. 1, the radiation source 104 can be any suitable radiation emitter capable of emitting broadband radiation or radiation in one or more desired wavelength bands. Although any range of radiation wavelengths that will be rapidly absorbed by the target and the underlying surface may be used, such as infrared and visible, the source 104 typically outputs energy in the wavelength range of from about 300 nm to about 700 nm in the visible wavelengths and 700 nm to 2 microns in the infrared region of the electromagnetic spectrum. Preferred radiation emitters include flash lamps, also known as strobes. In accordance with embodiments of the present invention, and as discussed in more detail below, the amount of energy provided at the sample substrate surface is considered, as opposed to just the cumulative or total energy output of the strobe, although this value is of interest in order to control the power source requirements for a portable, self-contained trace chemical detection system that includes both the stroboscopic signal amplification components and the detector.

The controller 124 is typically a microprocessor with volatile and/or nonvolatile memory. The controller 124 receives and responds to feedback from various sensors, if used, such as temperature sensors, voltage sensors, current sensors, and the like, as well as commands from a user. In addition, the controller issues appropriate control signals to system components. The controller 124 may further process measurement signals received from the detector 116 and interface with the user interface 128 to provide the measurements in a selected format to a user. For example, the controller 124 can apply calibration equations and scaling factors to convert signal magnitude into a measurement value and/or compare the signal magnitude and/or measurement value to predetermined thresholds to determine whether a target or non-target substance is present. The controller can also issue warning signals in the event of system malfunction.

The user interface 128 can be any suitable interface depending on the application. The interface 128 can provide audio and/or video feedback to the user. For example, the interface 128 can be an audio and/or visual and/or vibratory alarm when a target material is detected, a display identifying substances detected and their concentrations, a warning light that is illuminated when a target material is detected, and any combination of the foregoing. The user interface can also include user controls, such as buttons, toggles, switches, keys, and the like to provide user commands to the controller 124.

Figure 2:
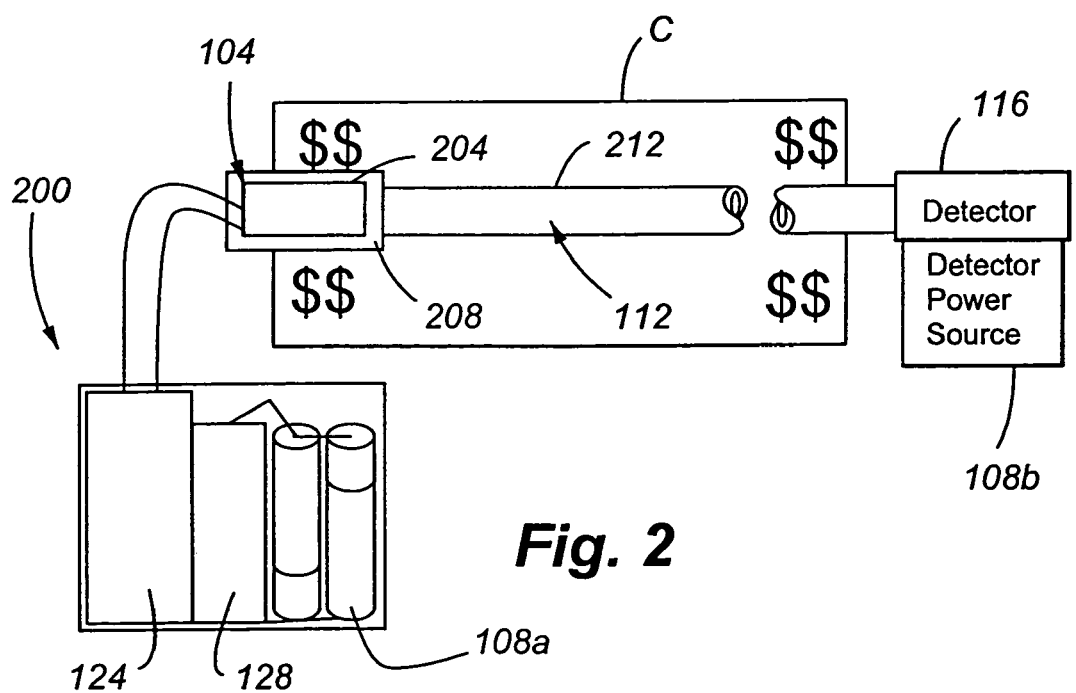
FIG. 2 is a top view of a stroboscopic signal amplification device used to obtain a sample from a note of currency.

Referring now to FIG. 2, an embodiment of the present invention is illustrated, wherein the device is used to obtain a sample from a document, and more particularly, from a note of currency C. The detection system 200 of FIG. 2 includes a radiation source 104 comprising a strobe light 204. In accordance with at least one embodiment of the present invention, and by way of example and not limitation, for effective low vapor pressure and particle desorption, a desired minimum energy at the sample surface is about 0.4 $J/cm^2$. Such energy per unit surface area value provides significant increase in the concentration of airborne compounds and/or particles from the sample, as compared to using a detector without strobe signal amplification.

Figure 13:
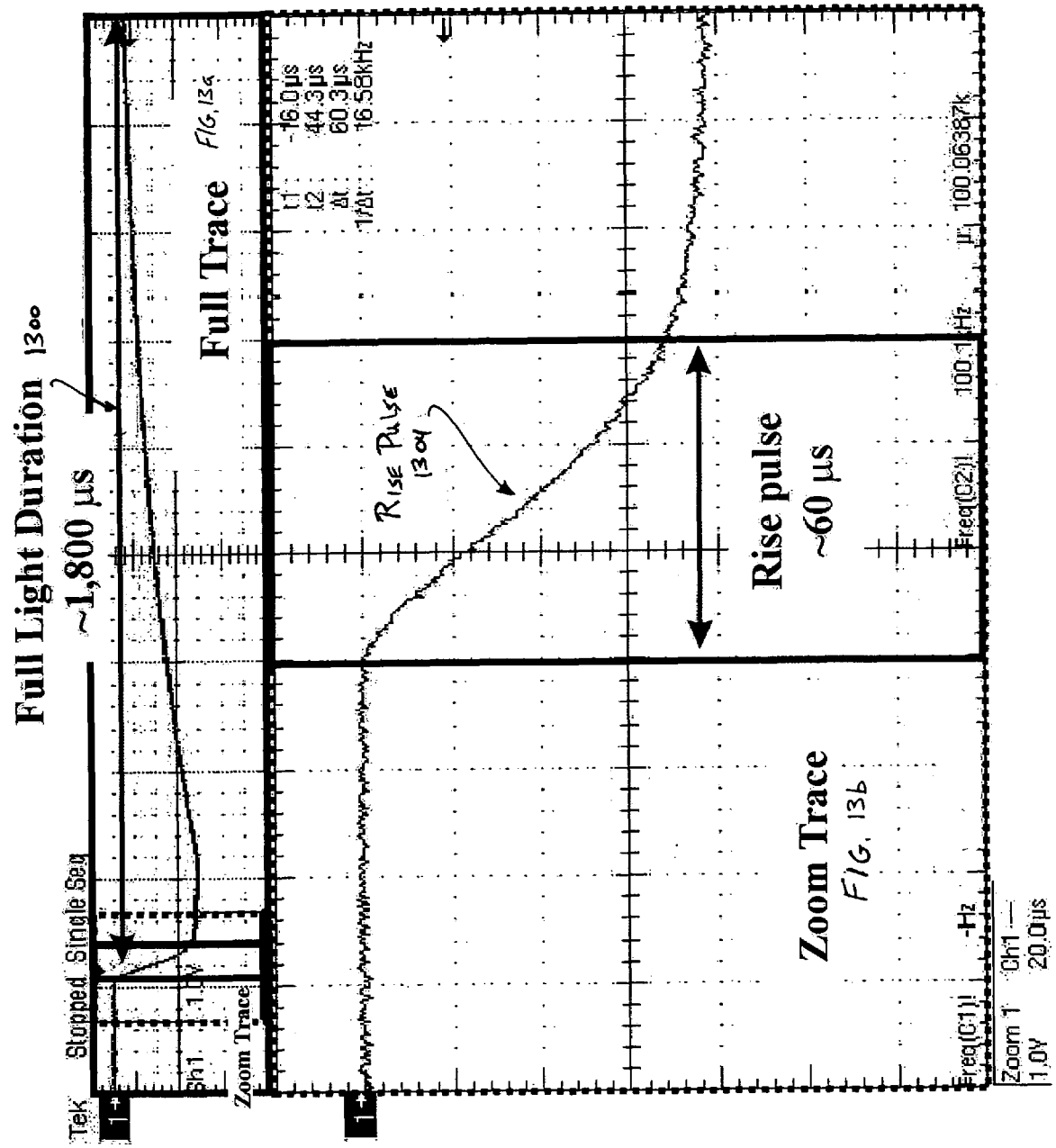
FIGS. 13a and 13b are full trace and zoom trace graphs, respectively, of illumination versus time for an example flash event in accordance with at least one embodiment of the present invention.

In terms of energy per area per time to peak discharge, that is, the initial time it takes for the strobe to go from zero to peak illumination flux, the value for the present invention is about 6 $mJ/cm^2/\mu s$, calculated as 0.4 $J/cm^2$ divided by 60 $\mu s$, where, in one embodiment, the peak illumination flux time is about 60 $\mu s$. However, embodiments of the present invention may operate with a time to peak discharge as low as about 5 $\mu s$, thereby yielding about 80 $mJ/cm^2/\mu s$ (calculated as 0.4 $J/cm^2$ divided by 5 $\mu s$) for the energy per area per time to peak discharge. As defined herein, the "time to peak discharge" or "rise pulse" means the duration of moving from zero illumination to maximum illumination where the sample surface and substrate are absorbing radiant energy. FIG. 13a illustrates a full trace for illumination detection of an experiment performed in accordance with at least one embodiment of the present invention. For the full trace shown in FIG. 13a, the full light duration 1300 extended about 1,800 $\mu s$. Other embodiments of the present invention may have a shorter full light duration or a full light duration of up to about 3000 $\mu s$, wherein the value of the full light duration depends on the amount of heating desired at the surface in combination with the intensity of the heating of the surface. FIG. 13b illustrates an enlarged view or zoom trace of the initial portion of the illumination example shown in FIG. 13a. For the zoom trace of FIG. 13b, the front-end duration of the discharge or rise pulse 1304 extends about 60 $\mu s$. It is noted that time to peak discharge or corresponding rise pulse for the strobe of the '804 patent is about 60 $\mu s$, which is significantly longer than the relatively low-energy strobe device of the present invention.

Of course other values are operable for the present invention other than those just described, and such other values are considered within the scope of the present invention, with the foregoing values provided for purposes of enablement and not to be limiting upon the scope of the claims. Thus, depending upon the type of sample surface being screened, at least 0.4 $J/cm^2$ of energy should be applied at the sample surface; however, higher levels are desirable, so long as the sample surface is not damaged. Accordingly, embodiments of the present invention should use an energy level at the sample surface that does not carbonize or burn the surface, and such levels are anticipated to be less than about 5 $J/cm^2$. Therefore, embodiments of the present invention should use an energy level at the sample surface preferably of between about 0.4 to 5.0 $J/cm^2$, and more preferably, between about 0.4 to 3.0 $J/cm^2$, and more preferably yet, between about 0.4 to 1.5 $J/cm^2$, wherein the lower levels just noted are more appropriate for portable devices that rely on a battery source, and wherein higher energy level devices just described can be used where an AC power source is nearby, provided the energy source is adjusted sufficiently low so as to cause little or no damage to the sample surface. Furthermore, in accordance with embodiments of the present invention, the time to peak discharge or rise pulse is preferably less than about 300 $\mu s$, and more preferably, less than about 200 $\mu s$, and more preferably yet, less than about 100 $\mu s$, and still more preferably yet, about 60 $\mu s$, with a low value of about 4 $\mu s$. The above noted values for energy level at the sample surface and time to peak discharge properly combine to provide sufficient heating of the sample surface with sufficient shock to the sample surface, while also not damaging the sample surface.

A reflector 208 may be used to direct the light generated from the strobe 204 to the sample surface. In accordance with at least one embodiment of the invention, the strobe 204 is positioned within a reflector 208, wherein the reflector 208 has a parabolic shape in side profile, and wherein the parabolic shape can be described by an equation $x^2=4py$, wherein p is preferably equal to one half the diameter of the flash lamp plus a gap to allow air circulation between the flash lamp and the reflector surface. In addition, if properly configured with a sampling port, the reflector 208 may optionally act as an airborne sample containment structure or shroud to temporarily isolate the sample area below the strobe and above the sample surface for collection and transport to one or more elements associated with the detector 116. Alternatively, the reflector 208 may be set at a standoff distance from the surface to be sampled, with a sample collection means situated proximate the sample surface for collection of liberated airborne compounds and particles.

The strobe 204 is preferably in electrical communication with a controller 124, wherein the strobe 204 and controller 124 are powered by a power source. For the detection system 200 of FIG. 2, a first power source 108a is interconnected to the controller 124, user interface 128, and strobe 204. In accordance with at least one embodiment of the invention, the power source 108a comprises one or more batteries, such a two AA batteries.

The detection system 200 further comprises a sample handling system 112 that comprises a tube 212 that leads to detector 116, wherein the sample handling system 112 and/or detector 116 include a means, such as a pump or fan, for generating a gaseous and particulate flow through the tube 212 in the vicinity of the strobe 204 and reflector 208. In accordance with at least one embodiment of the present invention, the tube 212 may include sample conditioning functionality, such a means for heating the airborne sample (for example, heat tape, hot air, etc.) within the tube 212 to prevent condensation of the sampled vapor from being deposited on the inner wall of the tube 212 during transport form the location of the sampled area to the detector 116. Thus, in accordance with embodiments of the invention, the present invention may include tubing, piping, and/or other conveyance structures for transporting an airborne sample comprising at least a portion of any volatilized high boiling point and/or low vapor pressure materials (or other sample particles, compounds, chemicals, elements, etc.) liberated from the sample surface through an inlet and through a heated conduit to the detector 116, wherein an internal surface of the heated conduit is maintained at a temperature sufficient to inhibit absorption and/or condensation of the high boiling point and/or low vapor pressure material on the internal surface of the tubing, piping and/or conveyance structures.

In accordance with the embodiment of the invention shown in FIG. 2, the detector 116 includes a second power source 108b. For the embodiment shown in FIG. 2, the controller 124 may be in communication with the detector 116, such as by a wireless communication device or by wiring.

Figure 3:
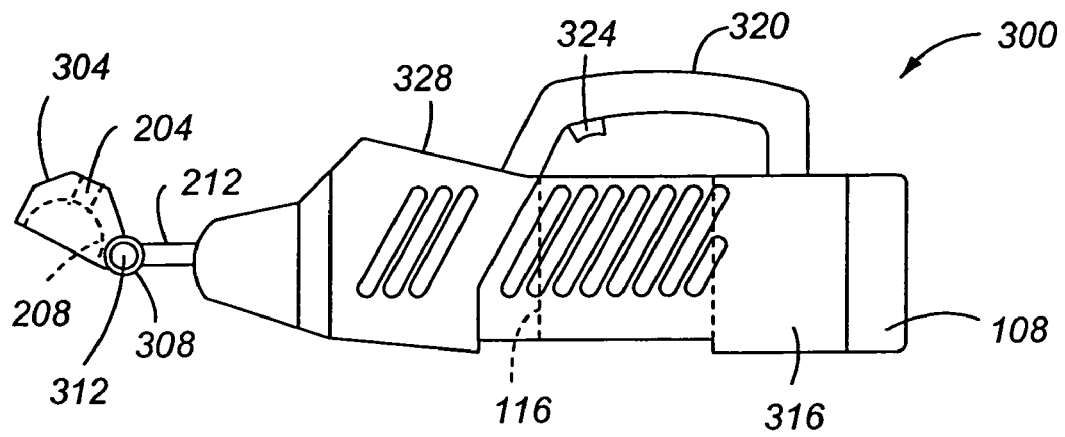
FIG. 3 is a side elevation view of a self-contained hand-held stroboscopic sampling apparatus in accordance with at least one embodiment of the present invention.

Referring now to FIG. 3, a portable detection system in the form of a handheld stroboscopic liberation or desorption apparatus 300 is shown. In accordance with at least one embodiment of the invention, the handheld stroboscopic desorption apparatus 300 includes a strobe 204 mounted within a sampling head 304 having a reflector 208, wherein the sampling head 304 can pivot about a swivel mechanism 308. The swivel mechanism 308 may include a spring 312 or other device for biasing the sampling head 304 in a downward direction so that the sampling head 304 is generally maintained in close proximity to the sample surface. The handheld stroboscopic desorption apparatus 300 preferably includes a tube 212 leading to a detector 116 that is located within a housing 316. In accordance with at least one embodiment of the invention, the housing 316 includes a handle 320 for manipulating the unit by the user. The handle 316 also preferably includes a trigger 324 for activating the unit. For portable usage, the handheld stroboscopic desorption apparatus 300 includes a power source 108 in the form of a battery pack for powering all of the unit's associated components, including the strobe 204 and the detector 116. Of course, the handheld stroboscopic desorption apparatus 300 may be interconnected to another separate power source, such as an AC outlet where the device is used in a location where electrical power is provided. The handheld stroboscopic desorption apparatus 300 also preferably includes a screen 328 as part of the user interface 128, wherein information is displayed to the user, as for example, the status of the strobe, the status of the detector and detector results.

In a separate aspect of the invention, the strobe 204 may flash a plurality of times during a single sampling event. For example, upon squeezing the trigger 324 once, the strobe 204 may emit two or more pulses or flashes of light spaced apart in time. The detector 116 may then report a single result for the sample generated and collected from the plurality of flashes. This method of providing a plurality of flashes for a single sampling event may be used for all of the various stroboscopic desorption devices of the present invention.

In use, the operator of the handheld stroboscopic desorption apparatus 300 manipulates the sampling head 304 into a position in relatively close proximity to a surface of interest, but not necessarily in contact with the surface. The user then activates the unit by pressing the trigger 324, thereby activating the strobe 204 and engaging the detector 116 to collect the sample and analyze the sample for substances of interest, such as explosive compounds and/or drugs.

Figure 4A:
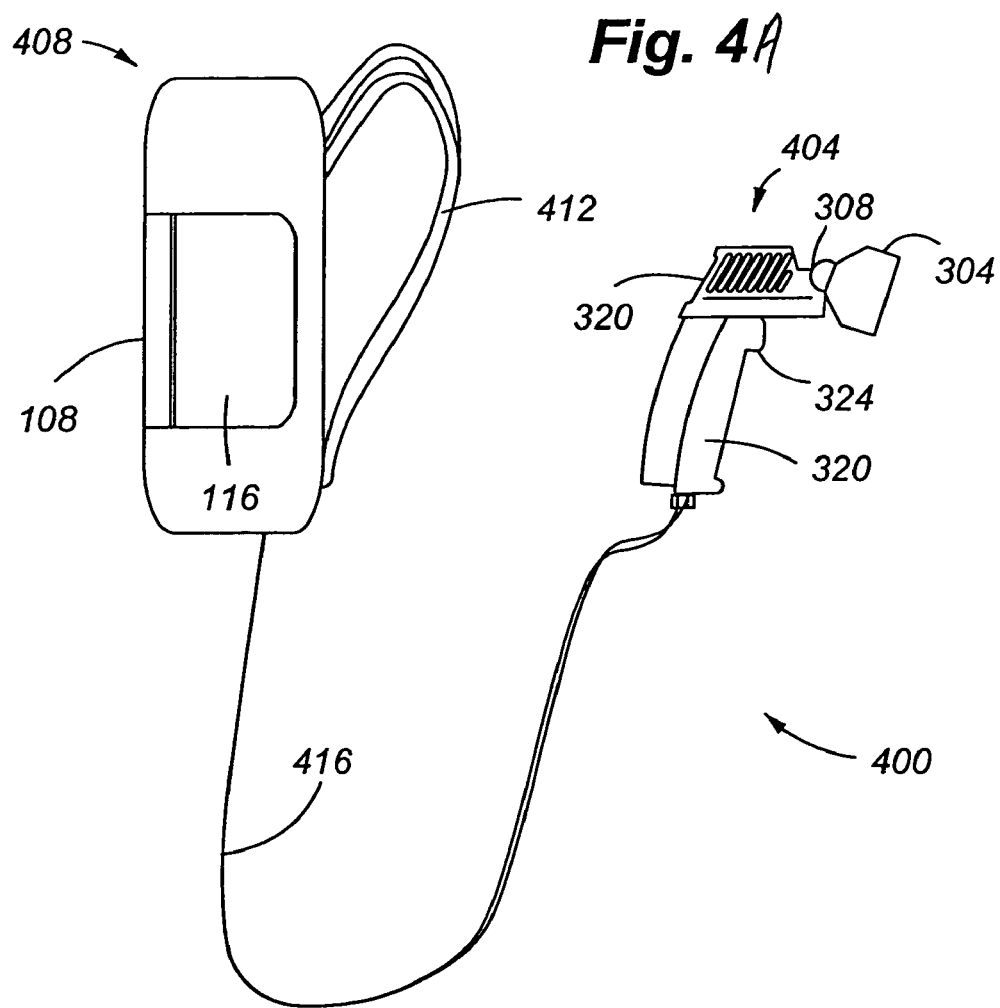
FIG. 4A is a side elevation view of a portable stroboscopic sampling apparatus in accordance with at least one embodiment of the present invention.

Referring now to FIG. 4A, and in accordance with at least one embodiment of the present invention, a portable detection system in the form of a wearable device or backpack stroboscopic desorption apparatus 400 is illustrated that comprises a handheld sampling wand 404 interconnected to a backpack portion 408 having straps 412. The backpack portion 408 preferably includes a detector 116 and a power source 108. An umbilical cord 416 interconnects the handheld sampling wand 404 to the backpack portion 408. The backpack stroboscopic desorption apparatus 400 with backpack portion 408 and wand 404 is particularly suited for field efforts and/or security operations, such as at security checkpoints. For example, the backpack stroboscopic desorption apparatus 400 may be used by a security person checking vehicles for explosives at a vehicle checkpoint. Here, the security person would be able to move around the vehicle and test a plurality of locations on the vehicle for traces of explosives or drugs. The backpack stroboscopic desorption apparatus 400 easily facilitates this use because the wand 404 can be used to check the exterior door handles and/or other exterior surfaces, such as the exterior opening panels of a compartment or trunk. Furthermore, the backpack stroboscopic desorption apparatus 400 can be used to also check at least portions of the vehicle's interior space by using the wand 404 to check upholstery, the steering wheel, glove box, arm rests and other interior surfaces and/or spaces as may be present.

Figure 4B:
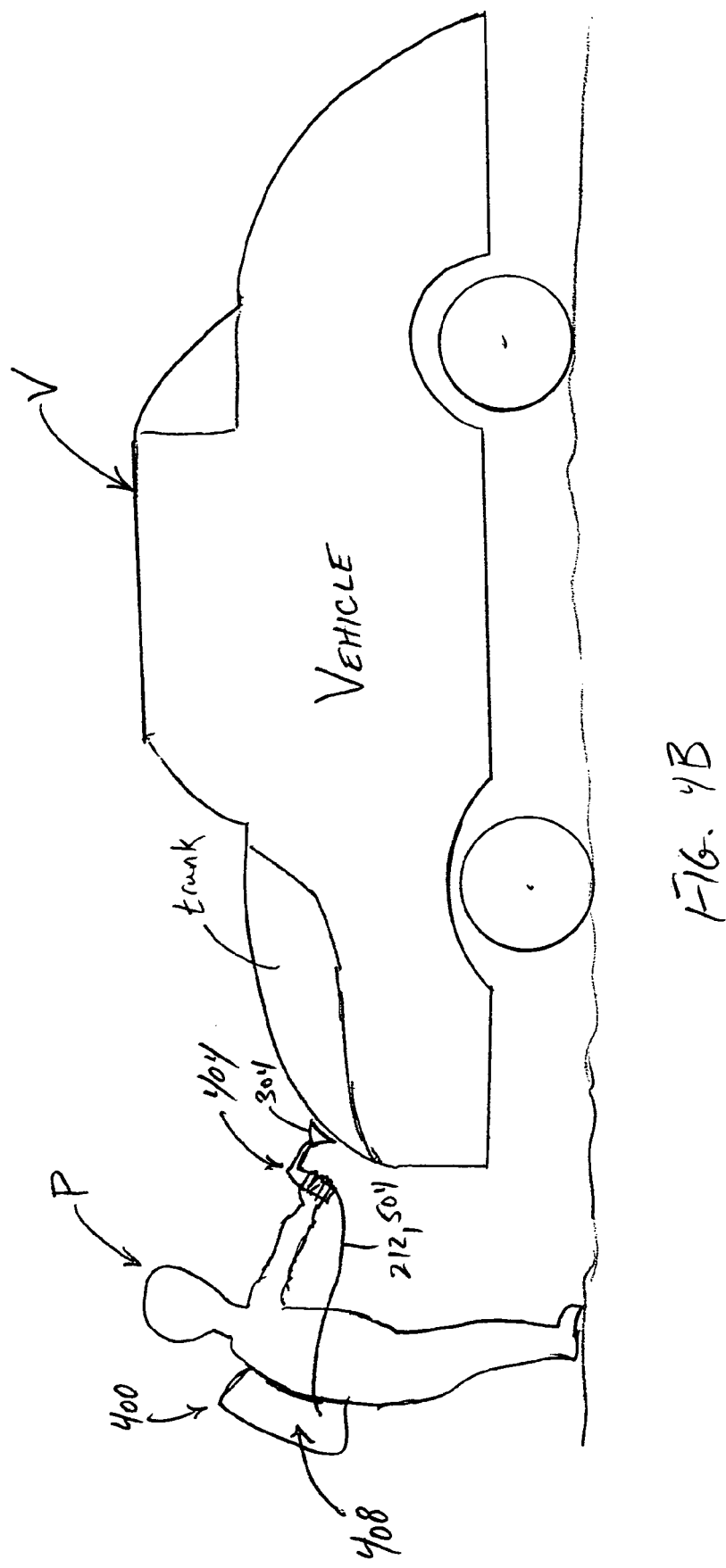
FIG. 4B is a side elevation view the apparatus of FIG. 4A in use by person scanning a surface of a vehicle.

Referring now to FIG. 4B, and in accordance with an embodiment of the invention, a person P is shown using backpack stroboscopic desorption apparatus 400 to scan a trunk area of a vehicle V. In use, the person is preferably wearing backpack 408 and holding the wand 404 substantially adjacent a surface of the vehicle V.

Figure 5:
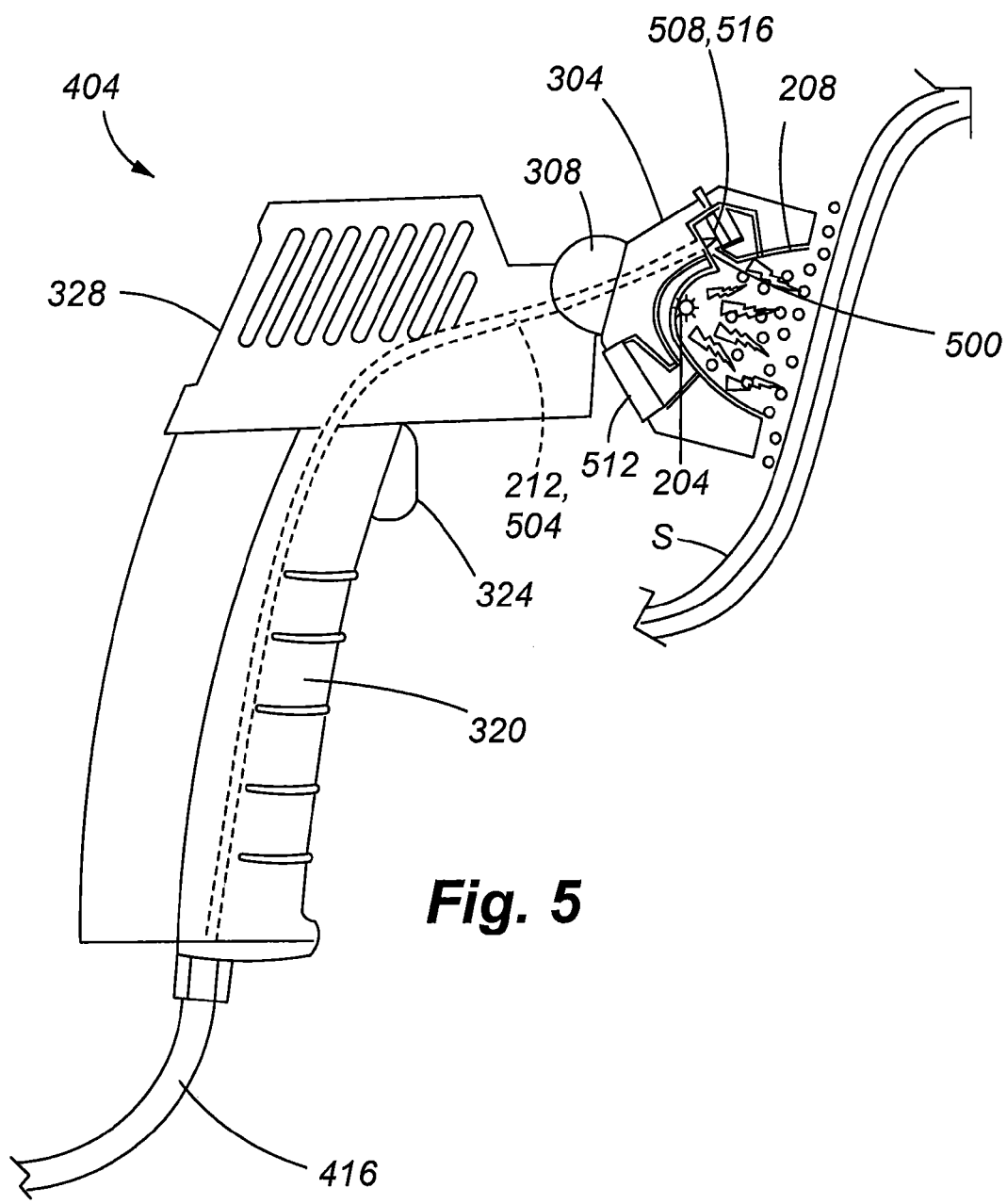
FIG. 5 is a side elevation view of a hand wand sampling device used with the apparatus shown in FIG. 4A, wherein the sampling head is shown in cut-away.

As best seen in FIG. 5, the umbilical cord 416 preferably includes fiber optic 504 and/or sampling tubing 212, as well as wiring for electrically connecting the wand 404 to the other components of the stroboscopic desorption apparatus 404 positioned in the backpack portion, such as the power source 108.

Referring now to FIG. 5, an enlarged view of the handheld sampling wand 404 is illustrated. In accordance with at least one embodiment of the present invention, the wand 404 includes a strobe 204 residing within a sampling head 304 that includes a parabolic shaped reflector 208. The wand 404 preferably includes a grip handle 320 with a trigger 324 for activating the unit to emit a strobe flash and collect a sample for analysis.

In accordance with at least one embodiment of the invention, an upper portion of the wand 404 preferably includes a screen 328 or other means for displaying information to the user. FIG. 5 also illustrates that the sampling head 304 is preferably positioned in relatively close proximity to the sample surface S. In at least one embodiment, a port 500 is provided in the reflector 208 of the sampling head for accessing the airborne sample after the flash from the strobe 204. A pump or fan 512 source may be provided to provide positive or negative pressure to pull the airborne sample toward the port 500. In one embodiment, the airborne sample is transmitted through tube 212 of the umbilical cord 416 to the backpack portion 408 for analysis by the detector 116. Alternatively, as discussed in more detail below, the airborne sample may be optically interrogated at the sampling head itself on a collection substrate 508, with data then transmitted to the detector 116.

In use, the operator of the backpack stroboscopic desorption apparatus 400 grasps the handheld sampling wand 404 and positions the sampling head 304 of the wand 404 adjacent the sampling surface S. The user then activates the strobe 204 by squeezing the trigger 324. The strobe 204 then flashes and the detector 116 of the backpack stroboscopic desorption apparatus 400 collects an airborne sample through a port 500 in the reflector 208 of the sampling head 304 for optical analysis at a collection surface 508 by the detector 116 located in the backpack portion 408.

There are at least four fundamental detector technologies that are amenable to implementation with stroboscopic signal amplification and that are in a product state that is robust and field portable, and still other detector systems are appropriate for more stationary detector locations. With regard to portable detectors, these detector technologies are Surface Enhanced Raman Spectroscopy (SERS), thermo-redox, chemiluminescence and ion mobility spectrometry (IMS). The three former systems spatially separate the sample activation and collection from the bulk of the detector and electronic subsystem. Accordingly, these systems are particularly adapted for use in a portable detection configuration, such backpack stroboscopic desorption apparatus 400. However, they may also be used in more stationary configurations that utilize stroboscopic desorption.

In SERS, the low vapor pressure compounds and particulates liberated using stroboscopic signal amplification are collected on a substrate surface located at the end of a fiber optic in close vicinity of the target surface. Referring again to FIG. 5, a fiber optic 504 may be provided between the sampling head 304 and the detector 116. In accordance with at least one embodiment of the present invention, the fiber optic 504 facilitates spectroscopic Analysis, such as ultra-violet, ultraviolet-visual light, infrared, Raman, luminescence, and fluorescence techniques. In at least one embodiment, the fiber optic 504 extends to the vicinity of port 500, wherein the airborne sample is pulled using a pump or fan 512 to the a SERS substrate surface 508 for optical scanning by the fiber optic 504. The detector 116 and its associated electronics may be up to several meters away, making the instrument ideal for an ergonomic backpack field instrument, such as system 400. In use, this makes for a very light and agile hand wand 404 for surface probing. Thus, one embodiment of the present invention comprises placing a strobe 204 for stroboscopic signal amplification in the vicinity of the sample surface S and/or fiber optic 504 associated with a SERS system. SERS has the advantage of being able to identify explosives via spectroscopic analyses and is able to match chemical signatures to internal libraries for conclusive identification without requiring a gas phase separation such as gas chromatography. InPhotonics of Norwood, Mass. currently manufactures SERS systems, and it is believed that such a system is readily adaptable for use with a stroboscopic liberation or desorption device of the present invention.

As noted above, another detection system appropriate for use with stroboscopic liberation or desorption is thermoredox. In thermo-redox, the compounds and particulates liberated using stroboscopic signal amplification are collected on a pre-concentrator 516 and pyrolyzed to release nitrous oxide, a key signature from explosive compounds. This sample collection and subsequent pyrolyzation may take place in the hand wand 404, if desired. The evolved nitrous oxide is then conveyed using tube 212 to the detector 116 located in backpack 408, where detection of compounds can be conducted using proprietary and conventional methods. For purposes of enablement, a Scintex EVD2500 is a ruggedized, hand portable unit that is believed to be appropriate for adaptation and use with a stroboscopic liberation or desorption device of the present invention.

As noted above, yet another detection system appropriate for use with stroboscopic liberation or desorption is chemiluminescence. In chemiluminescence, the compounds and particulates liberated using stroboscopic signal amplification are, like thermo-redox, collected on a preconcentrator 516 and pyrolyzed, but then exposed to a chemical reaction that creates an excited state of nitrous oxide that is detected using a very sensitive photometer. As with thermo-redox, it may be possible to move the pyrolysis produce to a backpack mounted system that performs the chemical reaction and optical detection. As with thermo-redox, chemiluminescence cannot identify the detected compounds unless the sampled vapor is subject to gas chromatography prior to pyrolysis.

In accordance with at least some embodiments of the present invention, the detector 116 may be mounted in a permanent location, such as in the vicinity of a baggage conveyor, as discussed below. Alternatively, a vehicle, such as a van may be adapted for transporting a detector 116 in accordance with embodiments of the present invention. For such configurations, trace detection of compounds such as explosives may be conducted using a mass spectrometer detector. Thus, there a variety of detection systems adaptable for use with stroboscopic desorption, including both portable and stationary detection systems.

In a separate aspect of the invention, a stroboscopic desorption device is provided for automatically examining baggage and/or packages. In one embodiment, a stroboscopic desorption device is used to screen luggage, packages, boxes, bags, (herein also collectively referred to simply as "baggage" or "luggage") as the luggage passes along a conveyor belt, conveyance mechanism, or other security check point. The device is positioned to bring a strobe desorption unit into sampling proximity with the surfaces of the luggage, thereby allowing multiple desorption events on each piece of luggage. As described herein, the strobe desorption unit may utilize one or more sensors.

Referring now to FIG. 6, and in accordance with at least one embodiment of the present invention, a first possible configuration of an automatic stroboscopic desorption and detection system 600 is shown for screening luggage and/or packages. The automatic stroboscopic desorption and detection system 600 preferably includes a conveyance system, such as one or more rollers, and/or one or more other continuous or endless sample feed mechanisms, such as a conveyor belt 604, that moves in the direction of arrow $A_1$, or otherwise conveys samples in the direction $A_1$. For the embodiment shown in FIG. 6, the conveyor belt 604 is used to automatically place test samples, such as packages, bags, and/or luggage, in testing proximity with one or more stroboscopic desorption devices 608. For the arrangement shown in FIG. 6, three stroboscopic desorption devices 608a, 608b and 608c are shown.

In the first configuration, the system 600 includes moveable radiation sources that extend over the width of a conveyor belt 604 that moves the luggage and/or packages. In at least one embodiment, a flap or hinged arm 612 is suspended from an upper hinge 616 that is separated a sufficient distance from the conveyor belt 604 to accommodate the largest pieces luggage L, bags or packages that may be encountered. The stroboscopic desorption devices 608a, 608b and 608c are preferably biased in a downward position to intercept the luggage L as it passes under the stroboscopic desorption devices 608a, 608b and 608c. Since the positioning apparatus preferably includes the hinged arm 612 that accommodates different size packages or luggage L, the hinge 616 allows rotation of the hinged arm 612 such that the stroboscopic desorption devices 608a, 608b and 608c can move up and down as a package or piece of luggage moves under it.

In at least one embodiment of the invention, the bottom of the flap or hinged arm 612 is preferably in sampling proximity with the conveyor belt 604, and the hinged arm 612 makes an oblique angle, such as an angle of approximately 45°, with the conveyor belt 604, such that the hinged arm 612 points downstream of the conveyor belt 604. In accordance with at least one embodiment of the present invention, there is a second hinge 620 at the trailing edge of the flap or hinged arm 612, to which is attached a second flap 624 that carries the desorption strobes and the analytical sensors if used, such as the SERS substrate surface. In at least one embodiment, this second flap 624 is the width of the conveyor belt 604 and is sized to allow the strobe 204 and SERS substrate surface 508 to screen the leading edge of luggage L that is lying flat.

The stroboscopic desorption devices 608a, 608b and 608c are consistent with the stroboscopic devices discussed earlier, and include a strobe 204 and detector 116 in communication with the sampling head of the stroboscopic desorption devices 608a, 608b and 608c. Of course, for a luggage conveyor or similar system located in a permanent structure with electrical power, the stroboscopic desorption devices 608a, 608b and 608c may be powered by AC electrical power. In addition, the liberation components, such as the sample head 304 and strobe 204, may be physically separated from the detector 116. For example, stroboscopic desorption devices 608a, 608b and 608c of FIG. 6 may provide a collective sample to a single detector. More particularly, for this and other embodiments of the invention, instead of immediately detecting the liberated sample, the liberated material may be collected on a preconcentrator (such as a length of packed column or a cooled piece of open tubular column) and later in time and/or at a different location, the collected material may then be desorbed for detection. Alternatively, the stroboscopic desorption devices 608a, 608b and 608c of FIG. 6 may each have their own detector 116. As shown in FIG. 6, if each of the stroboscopic desorption devices 608a, 608b and 608c have their own detectors 116, they may also be supplied with an individual alarm system 628 for notifying security personnel of the suspected piece of luggage L.

In at least one embodiment of the invention, an automatic sample conveyance and stroboscopic detection system may comprise a means for physically isolating, separating, and/or ejecting a suspected sample from the main conveyance mechanism, such as a suspected piece of baggage from a conveyor system, for quarantine or other special handling. For example, the conveyor belt 604 of system 600 may include one or more holding bins for detaining and/or quarantining a suspected piece of baggage after an initial detection using a detector, such as stroboscopic desorption device 608a. Such a feature may include a holding bin or isolation area positioned proximate or at a distance from the main conveyor belt 604, such that the suspected piece of baggage is automatically separated for further analysis and/or evaluation, such as by inspection by authorized personnel.

Referring now to FIGS. 7A-7C, a multi-hinge stroboscopic desorption system 700 is shown wherein the stroboscopic desorption device 704 is shown in its various positions. FIG. 7A shows the stroboscopic desorption device 704 in its at rest position with a piece of luggage L approaching it in direction arrow $A_1$. FIG. 7B shows the stroboscopic desorption device 704 rising along a side of the piece of luggage L. FIG. 7C shows the stroboscopic desorption device 704 along the top of the piece of luggage L.

As with the automatic stroboscopic desorption and detection system 600 discussed above, the multi-hinge stroboscopic desorption system 700 uses an apparatus, such as a conveyor belt, for automatically moving the sample item, such as a piece of luggage L, under the stroboscopic desorption device 704. The stroboscopic desorption device 704 preferably resides on a first flap 720 that is connected to a first hinge 708 that is capable of rising over the piece of luggage L. The first hinge 708 is interconnected to a preferably stationary second hinge 712, such as by second flap 716. Use of the first hinge 708 allows the sample head of the stroboscopic desorption device 704 to contact or come into sampling proximity with the sloped sides of the luggage L, while the second hinge 712 anchors the stroboscopic desorption device 704 while still accommodating rises in the stroboscopic desorption device 704 due to the size and shape of the luggage L. The stroboscopic desorption device 704 is consistent with the stroboscopic desorption devices discussed previously, and allows the surfaces of the subject article or luggage L to be tested with little or no damage to the surface of the article.

In use, the leading edge of luggage L traveling along the conveyor encounters the second flap 716 and lifts it. The stroboscopic desorption device 704 positioned along a first flap 720 hangs downwards bringing the strobe 204 and any attendant sensor, such as the SERS substrate surface 508, into sampling proximity with the leading side of the luggage L, such as is shown in FIG. 7B. In accordance with at least one embodiment, lifting the first flap 716 serves to actuate the sensor and the strobe 204 which flashes, as for example at 2 Hz. When the piece of luggage L baggage reaches the first hinge 708, the first flap 720 is lifted up and travels across the upper surface of the piece of luggage L.

Figure 8:
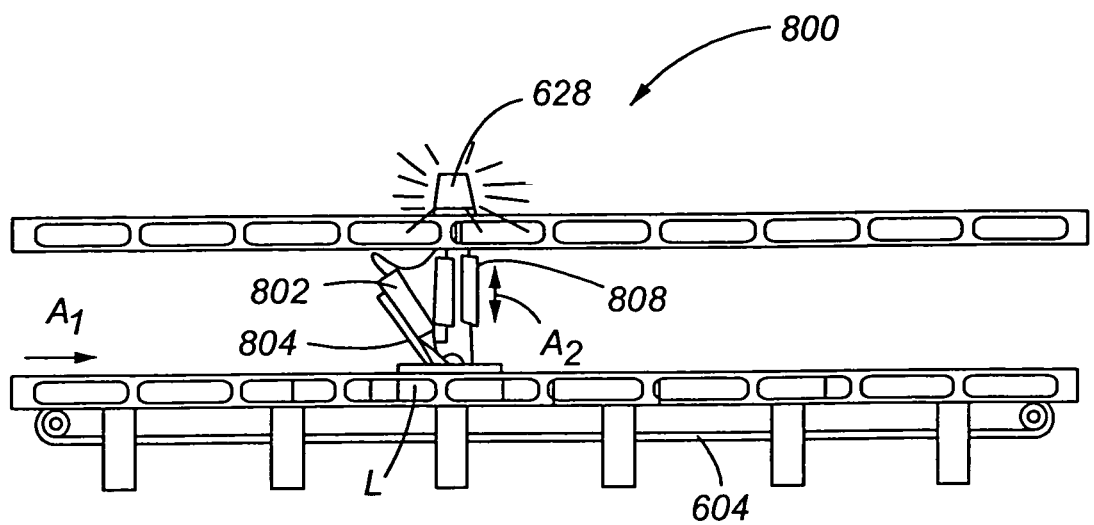

Referring now to FIG. 8, in an alternate embodiment of the present invention, an automatic stroboscopic desorption system 800 comprises a stroboscopic desorption device 802 having a strobe 204 and any attendant analytical sensor, such as SERS substrate surface 508 and fiber optic 504. The stroboscopic desorption device 802 is carried on a skid 804 that travels up and over the luggage L as it moves along the conveyor 604. A means for vertically lifting and lowering the system as per arrow $A_2$ is used to raise and lower the skid 804, wherein such means for raising a lowering may include a variety of mechanisms, such as hydraulic-damped springs, a pressure activated lift-assist, and/or optical activated lift-assist 808.

Figure 9A:
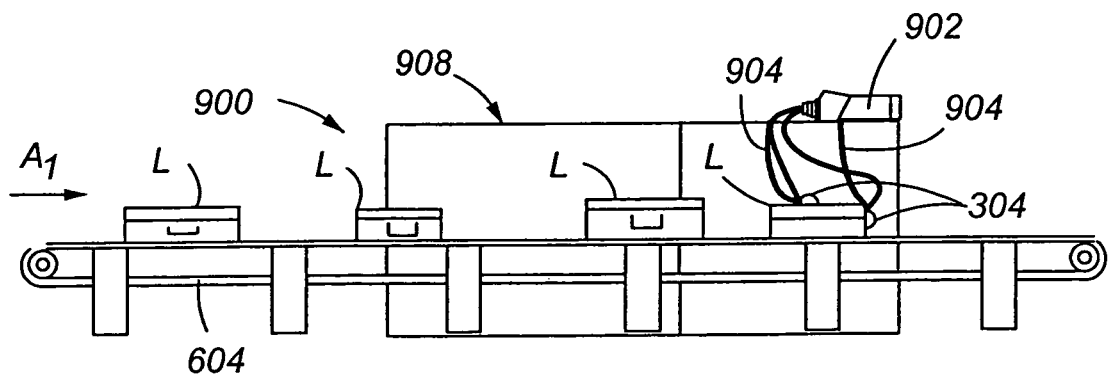

Referring now to FIG. 9A, yet an alternate embodiment of an automatic stroboscopic desorption system 900 is provided for use with X-ray machines at, for example, airline security check points. In at least one embodiment of the invention, the system 900 preferably uses a stroboscopic desorption device 902 having a plurality of strobes 204, and if applicable, sensors, such as SERS substrate surface 508 and fiber optic 504, that are carried on the flexible straps 904 that are on the entrance of a X-ray machines that protect passengers and TSA personnel from radiation emitted by the X-ray machine 908. As the luggage L passes through the curtain of straps 904, they drape over the luggage L pulling the sampling head 304 including strobe 204 and the attending sensors across the surface of the luggage L.

Referring now to FIG. 9B, and in accordance with at least one embodiment of the present invention, a stroboscopic desorption device 912 is shown wherein a plurality of sampling heads 304a-c are operatively interconnected to a single detector 116. The device 912 preferably includes a plurality of corresponding number of tubes 212a-c and/or fiber optics 504a-c, respectively, for transporting an airborne sample or conveying sample data to the detector 116. A valve 916 or other switching means may be used for isolating the sampling head and associated tubing or fiber optics for communication with the detector 116. Alternatively, the detector 116 may obtain sample data from all sampling heads 304a-c simultaneously. A detector using a plurality of sampling heads 304 is applicable to a number of embodiments described herein, including those for screening luggage or packages.

Referring now to FIG. 9C, and in accordance with at least one embodiment of the present invention, a graph 920 is shown that illustrates use of a means of isolating sample detection to an individual sampling head 304a-c. More particularly, and by way of example and not limitation, for a system using a pump or fan 512 for creating a preferential air or gas flow within a tube 212a-c, the pump or fan 512 is preferably switched "on" to provide suction to a first sampling head 304a, then the pump or fan 512 is allowed to continue operating during period Δt to clear the common tubing 212 and/or detector 116, then the fan or pump 512 is switch "on" to provide suction to a second sampling head 304b, and again, then the pump or fan 512 is allowed to continue operating during period Δt to clear the common tubing 212 and/or detector 116, and then the pump or fan 512 is preferably switched "on" to provide suction to a third sampling head 304c, then the pump or fan 512 is allowed to continue operating during period Δt to clear the common tubing 212 and/or detector 116. This is merely an example of an operation pattern. Accordingly it is to be understood that the system may be modified in a variety of ways, including re-ordering the switching, providing a different mechanism for flushing or clearing the sample head 304a-c and its associated tubing 212a-c. Furthermore, depending upon the detector used, for example, if fiber optics 504 are used with no tubing 212, little or no clearing or flushing may be required.

Figure 10:
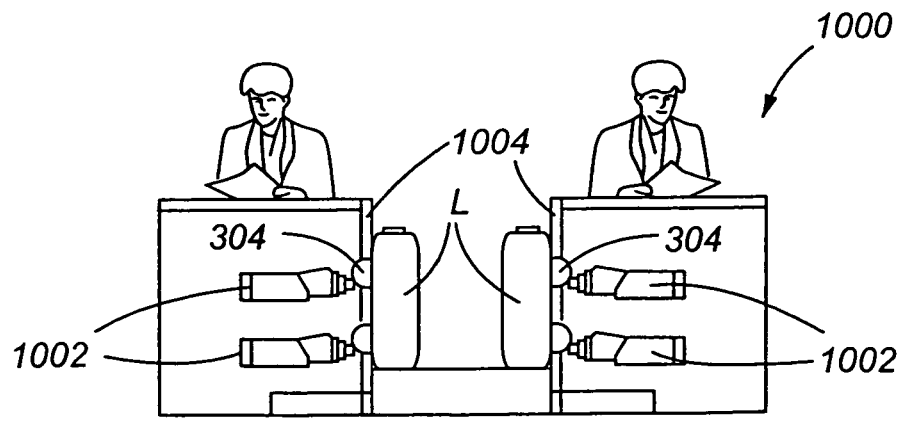
FIG. 10 is a view of another automated stroboscopic sampling systems in accordance with embodiments of the present invention.

Referring now to FIG. 10, in yet still another embodiment of the invention, an automatic stroboscopic desorption system 1000 is provided for use with airline check-in counters, or other similar package or luggage check-in stations. For the check-in automatic stroboscopic desorption system 1000, one or more stroboscopic desorption devices 1002 may be used, with the sampling head 304, including the strobe 204 and any attendant sensors built in to the sides of the scale or counter 1004. When the luggage L is placed next to the sampling head 304, the automatic stroboscopic desorption system 1000 allows the stroboscopic desorption device 1002 to screen the luggage L of compounds of interest, including explosives and/or drugs as the passenger is being checked-in.

Figure 11:
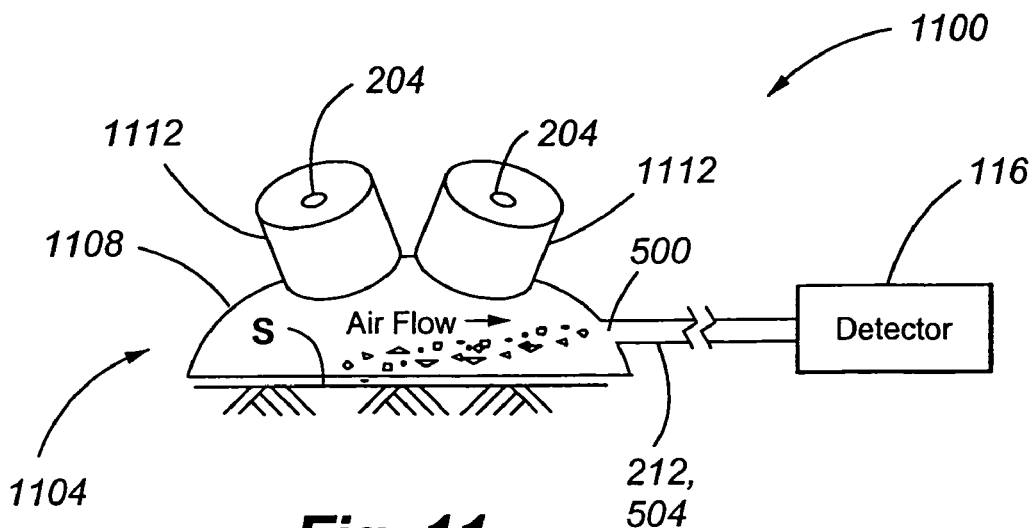
FIG. 11 is a side elevation view of a sampling head in accordance with at least one embodiment of the present invention.

Referring now to FIG. 11, a stroboscopic desorption system 1100 is shown that comprises sampling head 1104 having a shroud 1108 with a plurality of strobes 204. In at least one embodiment, each of the strobes 204 resides within a reflector 1112, wherein at least a portion of the reflector 1112 has a parabolic shape for directing the light from each strobe toward a common sample target area under the shroud 1108. This type of sampling head 1104 provides a means for providing multiple simultaneous energy sources directed at the same area of the sample surface S, or alternatively, it provides a means for temporally staggering the demand on a single strobe 204, thereby allowing each strobe capacitor to recharge, while the other strobe is tasked with radiating the sample surface S. The shroud 1108 preferably includes a port 500 leading to a sample tube 212 or fiber optic 504, that in turn leads to a detector 116.

Figure 12:
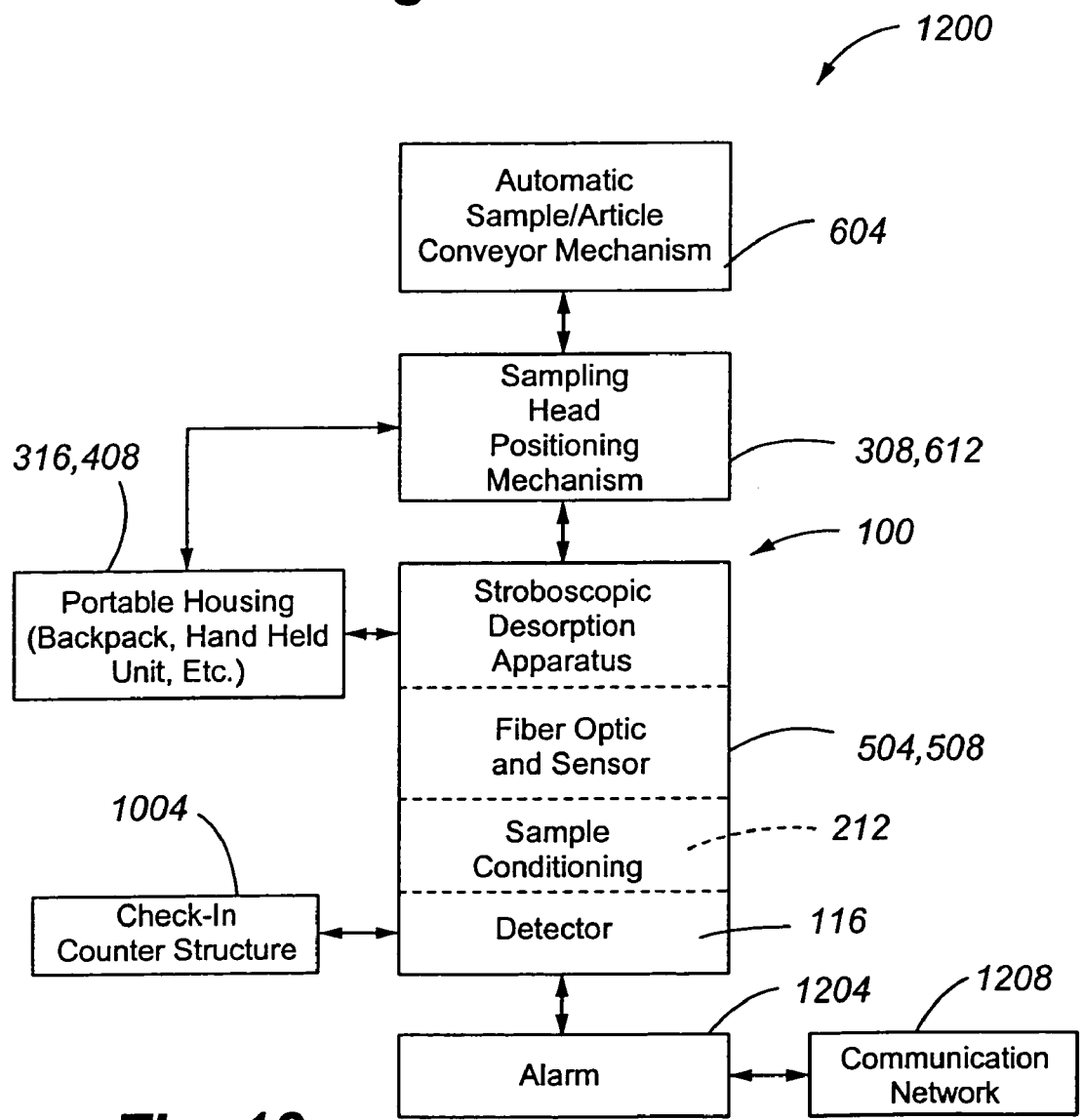
FIG. 12 is block diagram depicting several possible configurations of components from various embodiments of the present invention.

Referring now to FIG. 12, a block diagram showing several possible system configurations 1200 is illustrated. A stroboscopic desorption apparatus 100 may be combined with a fiber optic 504 and sensor 508 for transmitting sample information to a detector 116. The apparatus may also use sample conditioning, such as along a tube 212 to keep any vaporized portion of the sampled compounds from condensing prior to reaching the detector 116. In accordance with embodiments of the present invention, the sample conditioning may comprise a heated conduit or tube 212 to transport the collected sample to the detector. In at least one embodiment, the temperature of the heated conduit is at least the condensation temperature of the material. Where used, preferably the temperature of the heated conduit ranges from about 100° C. to about 250° C. In at least one embodiment, the heated conduit comprises a glass and/or ceramic surface adjacent the transported sample. In addition, when used, the heated conduit may comprise silanizing agent and/or a substantially nonpolar surface adjacent the transported sample.

Other possible system configurations include use of a sampling head positioning mechanism for placing the strobe in sampling proximity with a sample surface, wherein such mechanisms include a swivel mechanism 308 or hinged arm 612. In addition, an automatic sample/article conveyor mechanism such as a conveyor belt 604 may be used to place the sample under the strobe desorption apparatus. In accordance with embodiments of the present invention, the device may comprise a housing 316 or backpack 408 for providing a portable screening device, wherein the portable screening device is preferably a self-contained unit, including a power source 108 and a detector 116. Portions of the portable unit may include a sampling head, such as a hand-held wand interconnected to a backpack, wherein the wand portion includes a sampling head positioning mechanism, such as swivel mechanism 308. Alternatively, the apparatus may be stationary, such as located in a check-in counter 1004 at an airport terminal.

Referring still to FIG. 12, an alarm 1204 may be interconnected to the detector 116 associated with any of the embodiments described herein. In at least one embodiment, the alarm 1204 is either hardwired and/or wirelessly networked to a communication network 1208 for contacting authorities. Thus, a variety of different possible configurations are possible. In accordance with embodiments of the invention, the alarm 1204 and/or communication network 1208 may comprise wired transmission means, at least one wireless transmitter, and/or electronic recording means of the detection information. The detection information may be intermittently or continuously provided by the detectors of the present invention, such as the backpack stroboscopic desorption apparatus 400, to a separate location. This functionality provides for separate real-time or subsequent monitoring of screening results by offsite and/or spatially separated personnel (or monitoring by computer automation), and/or single or duplicate maintenance of records of testing results away from the actual detector unit in the event of the need, such as, for example, a security breach resulting from an infiltration of the security force by one or more opposition personnel. Such application may be used in a variety of situations, such as screening efforts at security checkpoints. The monitoring may further comprise ground positioning technology, as well as video recording of the subject and/or sample surface using a means for obtain video information, wherein this may comprise digital pictures taken directly by one or more computer chips positioned in the wand or other portion of the detector apparatus. This technology may be particularly useful for post-screening review of personnel and objects screened, with time tracking of the video to the detector results.

EXPERIMENTAL DATA

The following experimental data includes high-energy strobe results (Examples 1 and 2; provided for comparison purposes) and low-energy strobe results (Example 3, provided in support of the present invention).

Example 1

The apparatus used included a strobe light and an aluminum box with a sealed glass cover in which a sand sample was located. A valve was used to select a bypass or passage through the sample to a gas chromatograph. The sand sample included 1 ppm of triethyl phosphate and 1% by weight water. Triethyl phosphate is a high boiling point material, having a boiling point of 215° C.

A stream of air, having a flow rate of 64 ml/minute, was passed through the bypass and into the gas chromatograph with an open 3 mm stainless steel column and flame photometric detector fitted with a 526 nm optical filter for phosphorous detection. The baseline with the gas passing through the by pass was observed.

The gas flow was then switched to pass through the box and over the sand sample. There was no inflection in the baseline, indicating that the vapor pressure of the triethyl phosphate was too low to be detected. The detection limit for phosphorous is about $10^{-11}$ g/sec.

The strobe light was then placed over the cell and flashed. The detector showed an immediate response as a large peak. The strobe light was a SpeedotronicJ 2403J strobe head with a SpeedotronicJ BlacklineJ power supply, delivering 2,400 watt-seconds of power. A strobe head of this size can generate a very large electrical disturbance and, to ensure that the detector was, in fact, responding to the phosphorus and not an electrical signal, the glass of the cell was covered with cardboard and the strobe was again fired. There was no response from the detector.

Figure 14:
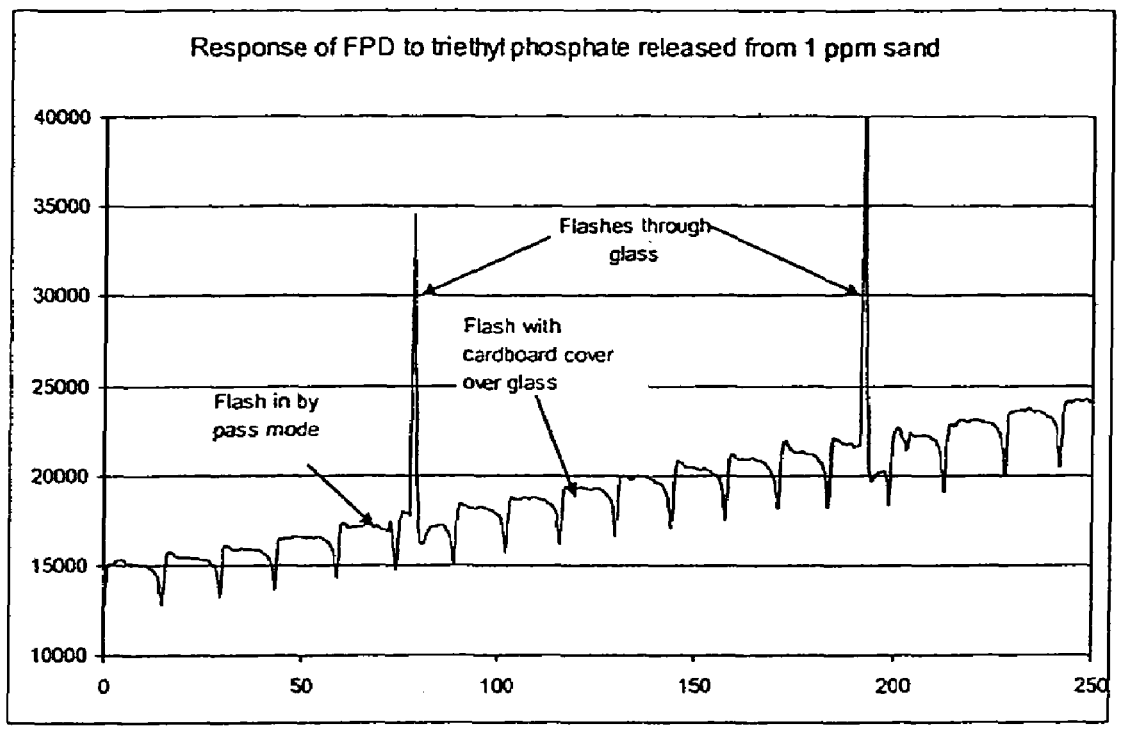
FIG. 14 is a plot of intensity (ion count) (vertical axis) versus scan number (horizontal axis) for an experiment as discussed in Example 1 herein.

The cover was removed from the box and the strobe was again fired. There was another large response from the detector. The output of this experiment is presented in FIG. 14. Referring to FIG. 14, the periodic signal from the detector is due to the thermal cycling of the heater in the detector.

This experiment shows that the test apparatus can successfully detect extremely low concentrations of a high boiling point substance.

Example 2

The apparatus included a 1,200 Joule strobe lamp, a heated inlet, an atmospheric pressure chemical ionization tandem mass spectrometer, and a test rig containing TNT impregnated sand. The test rig was a cylindrical test cell with a glass cover. Air was drawn through the apparatus and into the inlet system of the spectrometer. The spectrometer was set to monitor the response of the molecular ion of TNT at a mass to charge ratio (m/z) of 227.

Figure 15:
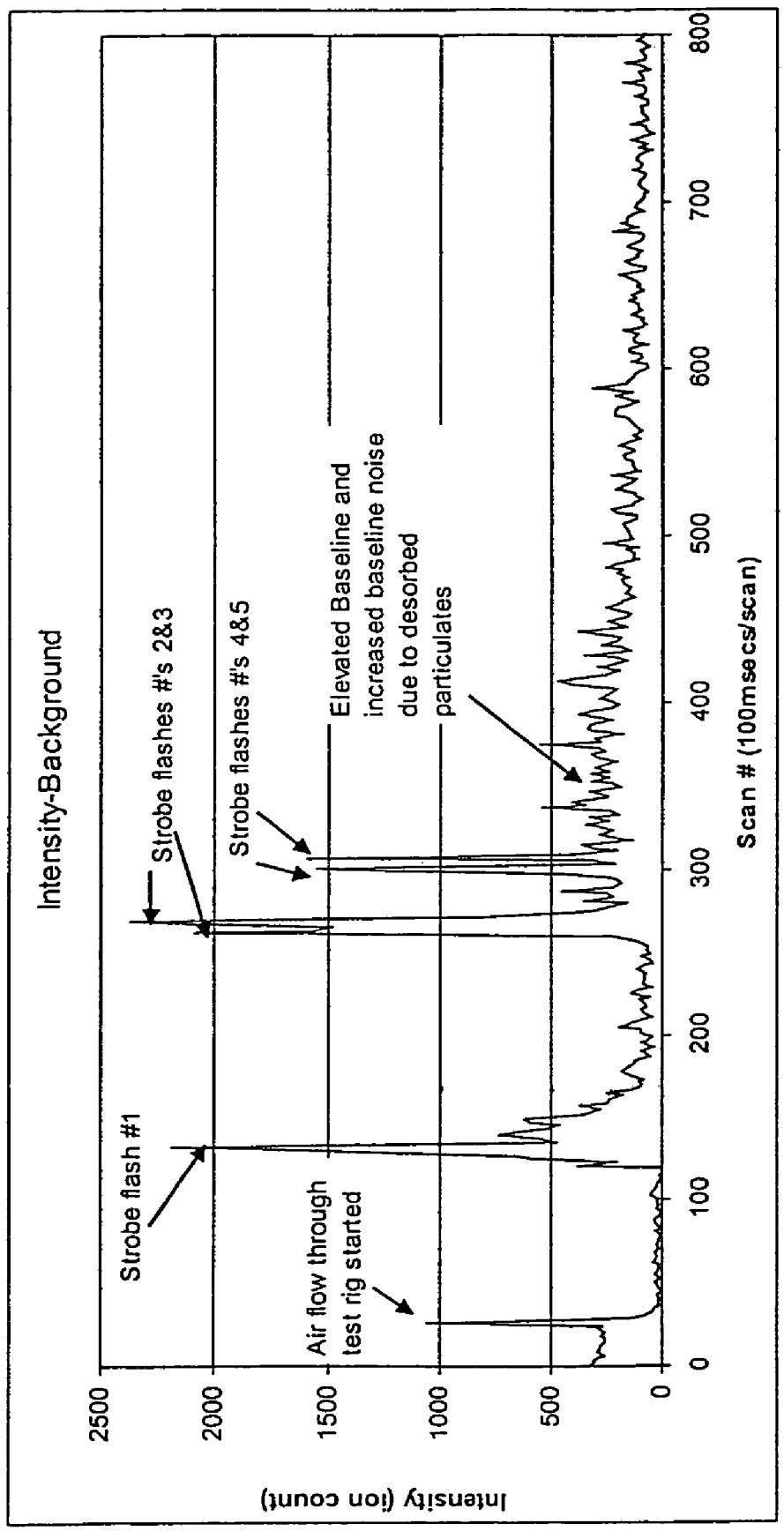
FIG. 15 is a plot of intensity (ion count) (vertical axis) versus scan number (horizontal axis) for an experiment as discussed in Example 2 herein.

The results of one of these experiments are presented in FIG. 15. The mass chromatogram of FIG. 15 illustrates the release of a series of sharply defined plumes of vapor in response to the influx of energy from the strobe. It is also apparent that the baseline after the first strobe flash becomes elevated and analytically much noisier. It is assumed that this increase in the baseline activity is due to explosive carrying particulate material that has been released from the soil by the strobe. This activity increases with the subsequent flashes due to the sand being dried by the heat of the strobe and becoming more prone to release fine particulates.

Example 3

In view of the strong response that was observed with high-power (+1,200 J) strobes, it was decided to test the response of lower-powered strobes in the range of 3-6 Joules. Although the output from these small strobes is much less, the area that they illuminate is also much smaller so that the Joules/cm$^2$ may still be substantial from a signal amplification perspective, but not damaging to the subject surface.

The sensor used for these tests relies upon a fluorescent polymer that is quenched by nitroaromatics such as TNT. The response of the sensor when a nitroaromatic is detected is a quench in the fluorescent response, resulting in a trough in the baseline. The sensor is very sensitive and detection limits as low as one femtogram are claimed.

A series of tests were conducted using pieces of canvas that had been impregnated with varying quantities of TNT. The TNT was introduced onto the canvas from PTFE strips that had been prepared by pipetting TNT in solution onto the strips, and allowing the solvent to evaporate. The residual solid TNT was then transferred to the canvas by carefully wiping the explosive onto the cloth. The canvas strips were then exposed to a flash from a 4.2 Joule strobe, while drawing the evolved plume into the sensor. The tests were repeated in triplicate and with varying quantities of TNT.

The results of the tests are shown in FIG. 16. It can be seen that with 5 µg or 1 µg of TNT, the fluorescence is almost totally quenched and, therefore, the detector is saturated. The detection limit from these tests was approximately 0.01 µg of TNT. This was a surprising and unexpected result from a small strobe, because earlier work had shown that decreasing the power of a high-powered strobe from 2,400 J to 1,200 J resulted in a dramatic decrease in the response from the detector.

A number of variations and modifications of the invention can be used. It would be possible to provide for some features of the invention without providing others. For example in one alternative embodiment, the system is used to detect low boiling point or high vapor pressure materials. In another alternative embodiment, multiple detectors can be used simultaneously or near simultaneously to detect different target substances.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights that include alternative embodiments to the extent permitted, including alternate, interchangeable and/or equivalent structures, functions, ranges or steps to those claimed.

What is claimed is:

1. A method, comprising:
    irradiating simultaneously, by a first strobe and during a sample period, a sample surface with a plurality of different wavelengths of electromagnetic radiation, the sample surface comprising a target material located on the sample surface, the target material being at least one of a micron and sub-micron particle, wherein the particle is dislodged from the sample surface by the electromagnetic energy, wherein the target material is not pyrolyzed by the electromagnetic radiation and wherein the electromagnetic energy irradiated during the sample period has the following characteristics:
        from about 0.4 to about 5 Joules of electromagnetic energy per square centimeter of the sample surface area as measured at the sample surface,
        a plurality of different wavelengths in a range of from about 300 nm to about 2 microns, and
        a time to peak discharge or rise pulse less than about 300 µs; and
    collecting an airborne sample comprising the target material; and
    detecting the presence of the target material in the collected airborne sample.

2. The method of claim 1, wherein the target material is dislodged from the sample surface in the absence of ultrasonic vibrations and air bursts and wherein a full duration of irradiation of the sample surface is no more than about 3,000 µs.

3. The method of claim 2, wherein the strobe is operated discontinuously and wherein the full duration is no more than about 1,800 µs.

4. A method, comprising:
    (a) irradiating simultaneously, by a first strobe and during a sample period, a sample surface with electromagnetic radiation having a plurality of different wavelengths, the sample surface comprising at least one target material located on the sample surface, wherein the electromagnetic energy irradiated during the sample period has the following characteristics:
        (A1) from about 0.4 to 5 Joules of electromagnetic energy per square centimeter of the sample surface area as measured at the sample surface,
        (A2) a range of different wavelengths comprising wavelengths in a range of from about 300 nm to about 2 microns,
        (A3) a time to peak discharge or rise pulse less than about 300 µs, and
        (A4) a full duration of up to about 3,000 µs, wherein said energy volatilizes the at least one target material from the sample surface; and
    (b) detecting, by a detector, the presence of the at least one target material after volatilization by said electromagnetic energy.

5. The method as claimed in claim 4, wherein at least a portion of said electromagnetic energy is transmitted to the sample surface during an initial discharge peak interval of less than about 100 microseconds and wherein the full duration is no more than about 1,800 µs.

6. The method as claimed in claim 4, wherein the first strobe is positioned within a reflector, the reflector having a parabolic shape in side profile, the parabolic shape described by an equation $x^2=4py$, wherein p=at least one half of the diameter of the flash lamp.

7. The method as claimed in claim 4, further comprising:
    sampling, by a sampling mechanism, at least one of an airborne particle and compound associated with the at least one material, the sampling mechanism being in communication with the detector.

8. The method as claimed in claim 7, wherein the target material is at least one of a micron and sub-micron particle and wherein the particle is dislodged from the sample surface by the electromagnetic energy.

9. The method as claimed in claim 7, wherein said detector comprises a fiber optic.

10. The method as claimed in claim 4, wherein said detector is selected from the group consisting of spectroscopy, thermo-redox, chemiluminescence, and spectrometry and wherein the at least one target material is volatilized from the sample surface for detection in the absence of ultrasonic vibrations and air bursts.

11. The method as claimed in claim 4, wherein said detector comprises surface enhanced Raman spectroscopy.

12. The method as claimed in claim 4, further comprising a second strobe located proximate said first strobe and directed at the sample surface, wherein the first and second strobes are operatively associated with a common shroud and wherein the first and second strobes are operated discontinuously.

13. The system as claimed in claim 4, wherein said system is operatively associated with a conveyance mechanism for moving said sample surface from a first position to a second position, wherein said first position is not in sampling proximity of the first strobe and wherein said second position is in sampling proximity with the first strobe.

14. The method as claimed in claim 4, wherein said first strobe is interconnected to a hand wand, said hand wand spaced apart from at least a portion of said detector.

15. The method as claimed in claim 4, wherein said first strobe is interconnected to sampling head, said sampling head operatively associated with at least one of a handle, a hand wand, a check-in counter, an X-ray machine, a conveyance mechanism, a conveyor belt, a flap, a floor, a sample container, a vehicle, a biasing member, and a hinged arm.

16. The method as claimed in claim 4, further comprising: a preconcentrator interconnected to the detector.

17. The method as claimed in claim 4, wherein the target material is selected from the group consisting essentially of:
   an explosive compound;
   an explosive related compound;
   a chemical warfare agent;
   a drug;
   an industrial compound;
   a toxic industrial compound; and
   mixtures thereof.

18. The system as claimed in claim 4, wherein the target material is a drug selected from the group consisting essentially of:
   cocaine;
   heroin;
   opium;
   marijuana;
   methamphetamines;
   lysergic acid diethylamide; and
   mixtures thereof.

19. The system as claimed in claim 4, wherein the target material is an explosive compound selected from the group consisting essentially of:
   trinitrotoluene;
   dinitrotoluene;
   2-ADNT;
   4-ADNT;
   nitroglycerine;
   ammonium nitrate;
   acetylides of copper;
   acetylides of silver;
   mercury fulminate;
   lead azide;
   diazodinitrophenol;
   nitrosoguanidine;
   lead styphnate;
   cyclotrimethylenetrinatramine;
   pentaerythritol tetranitrate;
   triacetone triperoxide;
   dynamite;
   semtex;
   EGDN;
   DMNB;
   H-6;
   C-4;
   picric acid;
   nitrocellulose; and
   mixtures thereof.

20. The method as claimed in claim 4, wherein the strobe does not pyrolyze the target material during irradiation of the sample surface.

21. The method as claimed in claim 4, further comprising a collector surface to collect the volatilized target material, wherein the collector surface is thereafter contacted with electromagnetic energy to pyrolyze the target material for input into the detector.

* * * * *